(12) United States Patent
McPeek

(10) Patent No.: US 9,983,311 B2
(45) Date of Patent: May 29, 2018

(54) MODULAR SYSTEMS AND METHODS FOR DETERMINING CROP YIELDS WITH HIGH RESOLUTION GEO-REFERENCED SENSORS

(71) Applicant: AGERPOINT, INC., New Smyrna Beach, FL (US)

(72) Inventor: K. Thomas McPeek, Orlando, FL (US)

(73) Assignee: AGERpoint, Inc., Daytona Beach, FL (US)

( * ) Notice: Subject to any disclaimer, the term of this patent is extended or adjusted under 35 U.S.C. 154(b) by 0 days. days.

(21) Appl. No.: 15/418,562

(22) Filed: Jan. 27, 2017

(65) Prior Publication Data

US 2017/0176595 A1 Jun. 22, 2017

Related U.S. Application Data

(63) Continuation of application No. 15/209,689, filed on Jul. 13, 2016.

(60) Provisional application No. 62/192,031, filed on Jul. 13, 2015.

(51) Int. Cl.
*G01S 17/89* (2006.01)
*A01D 41/127* (2006.01)
(Continued)

(52) U.S. Cl.
CPC ........... *G01S 17/89* (2013.01); *A01D 41/127* (2013.01); *G01C 21/165* (2013.01); *G01F 22/00* (2013.01);
(Continued)

(58) Field of Classification Search
USPC .......................................................... 702/5
See application file for complete search history.

(56) References Cited

U.S. PATENT DOCUMENTS

2004/0136139 A1* 7/2004 Kummel ............. A01M 7/0089
361/226
2005/0084176 A1* 4/2005 Talapov ............... A61B 5/0062
382/286
(Continued)

OTHER PUBLICATIONS

Chang et al., "The performance analysis of a real-time integrated INS/GPS vehicle navigation system with abnormal GPS measurement elimination." In: Sensors. Aug. 15, 2013 (Aug. 15, 2013) Retrieved from <https://www.researchgate.net/profile/Kai_Wei_Chiang/publication/255975937_The-Performance_Analysis_of_a_Real-Time_Integrated_INSGPS_Vehicle_Navigation_System_with_Abnormal_GPS_Measurement_Elimination/links/568d289308aec2fdf6f6dffe.pdf>.

(Continued)

*Primary Examiner* — Gregory J Toatley
*Assistant Examiner* — Terence Stifter, Jr.
(74) *Attorney, Agent, or Firm* — Bryan Cave LLP

(57) ABSTRACT

Systems, and methods for controlling a modular system for improved real-time yield monitoring and sensor fusion of crops in an orchard are disclosed. According to some embodiments of the invention, a modular system for improved real-time yield monitoring and sensor fusion may include a collection vehicle, a modular processing unit, a volume measurement module, a three-dimensional point-cloud scanning module, an inertial navigation system, and a post-processing server. As the collection vehicle travels through an orchard, the volume measurement module calculates volume measurements of the windrow, the three-dimensional point-cloud scanning module assembles point-clouds of each plant in the orchard, and the inertial navigation system calculates geodetic positions of the collection vehicle. The modular processing unit may fuse the collected data together and transmit the fused data set to a post-processing server. The post-processing server may process the geodetic position data for errors which may be used for geo-referencing the fused data.

18 Claims, 12 Drawing Sheets

(51) Int. Cl.
*G01S 7/486* (2006.01)
*G01N 33/02* (2006.01)
*G01S 13/86* (2006.01)
*G01S 17/02* (2006.01)
*G01N 21/17* (2006.01)
*G01F 22/00* (2006.01)
*G01C 21/16* (2006.01)
*G01S 17/88* (2006.01)
*G01N 33/00* (2006.01)

(52) U.S. Cl.
CPC .......... *G01N 33/025* (2013.01); *G01S 7/4865* (2013.01); *A01D 41/1277* (2013.01); *G01N 33/0098* (2013.01); *G01N 2021/1797* (2013.01); *G01S 13/867* (2013.01); *G01S 17/023* (2013.01); *G01S 17/88* (2013.01)

(56) References Cited

U.S. PATENT DOCUMENTS

| | | | | |
|---|---|---|---|---|
| 2011/0282622 A1* | 11/2011 | Canter | ............... | G06K 9/00691 702/150 |
| 2013/0100114 A1* | 4/2013 | Lynch | ................ | G01C 21/3638 345/419 |
| 2013/0124239 A1 | 5/2013 | Rosa et al. | | |
| 2013/0325346 A1* | 12/2013 | McPeek | ............ | G01N 33/0098 702/2 |
| 2014/0267357 A1* | 9/2014 | Tartaglia | ................. | G06T 11/40 345/589 |
| 2015/0379721 A1* | 12/2015 | Good | .................... | G06T 7/0075 348/47 |
| 2016/0370208 A1* | 12/2016 | Patel | ....................... | G01D 9/38 |

OTHER PUBLICATIONS

Zhang et al., "Mapping orchards for autonomous navigation." In: American Society of Agricultural and Biological Engineers. Jul. 16, 2014 (Jul. 15, 2014) Retrieved from <https://www.ri.cmu.edu/pub_files/2014/7/ASABE_2014.pdf>.

Notification of Transmittal of the International Search Report and the Written Opinion of the International Searching Authority, or the Declaration and the International Search Report and Written Opinion in PCT/US2016/042161, dated Oct. 4, 2016.

* cited by examiner

MODULAR SYSTEMS AND METHODS FOR DETERMINING CROP YIELDS WITH HIGH RESOLUTION GEO-REFERENCED SENSORS

CROSS-REFERENCE TO RELATED APPLICATIONS

The present application is a continuation application of U.S. patent application Ser. No. 15/209,689 filed on Jul. 13, 2016, which claims priority to U.S. Provisional Patent Application No. 62/192,031 filed on Jul. 13, 2015. The entire contents of the above applications are incorporated by reference as if recited in full herein. The present application is related to U.S. patent application Ser. No. 13/907,147 filed on Jun. 1, 2012 which is also incorporated herein by reference in its entirety.

TECHNICAL FIELD

The present invention is related to agricultural analysis, and more particularly, to systems and methods for determining the crop yields of windrows based on geo-referenced sensor measurements using a modular system of sensors including LiDAR and weight sensors.

BACKGROUND

Windrow harvesting typically involves sweeping nuts, grains or similar small crops into long rows on a field for drying. For example, after nuts are shaken from trees in an orchard, they are typically swept into windrows three to four feet wide. Harvesters then typically condition the windrows by re-sweeping the rows, removing debris such as rocks or branches. Harvesters then typically collect the crops and bring them to a storage.

In some orchards, growers may add yield monitoring devices to their harvesters, tractors, or similar agricultural vehicles for the precision monitoring of agricultural crops. Yield monitoring devices typically measure the total amount of crop harvested in a windrow by measuring several attributes of the crop as it passes through the device. For example, sensors in a grain yield monitor may measure the total grain harvested by measuring the grain mass flow, moisture content, and the speed of the grain as it passes through the elevator and holding tank of a harvester.

Although some yield monitoring devices have been integrated with GPS devices to associate the yields with geographic information, yield monitoring devices generally do not associate yield with a particular plant. As a result, growers have not been able to fully determine how factors such as environment and disease have or will affect the yield of that plant, and on a larger scale, the orchard as a whole.

Further, the sensors typically used in yield monitoring devices are generally expensive and inaccurate. For example, to measure mass flow of grains passing through a harvester, yield monitoring devices typically use impact plates and load cells. Other yield monitoring devices may also use passive sensors to measure and process ambient light reflected from the measured objects. However, passive sensors are not typically accurate for taking spectral measurements in the field. Typically, inexpensive optical sensors, such as LED sensors, have not been used in precision farming applications because of their low resolution.

Accordingly, a need exists for a low-cost, optically-based yield monitoring device that associates yield with a particular plant or region within a grower's holdings. In particular, a need exists for accurately estimating yield measurements, such as volume, and associating such measurements with high-resolution and precise geodetic positional data.

SUMMARY

In various embodiments, the invention provides systems, methods, and apparatuses for controlling a modular system for improved real-time yield monitoring and sensor fusion of crops in an orchard. According to some embodiments of the invention, a modular system for improved real-time yield monitoring and sensor fusion includes a collection vehicle, a modular processing unit, a volume measurement module, a three-dimensional point-cloud scanning module, an inertial navigation system, and a post-processing server. The modular processing unit, volume measurement module, three-dimensional point-cloud scanning module, and inertial navigation system may have clocks that are used to generate time-stamps, and fuse the data collected by each sensor.

The collection vehicle may transport modular sensors through rows of plants in an orchard. As the collection vehicle travels through the rows in the orchard, the volume measurement module measures the volume of a windrow formed in the row using a Light Detection and Ranging ("LiDAR") sensor. The volume measurement module calculates the volume by laterally scanning the windrow formed in a row of the orchard every distance d traveled by the collection vehicle. The lateral scan is an emission of a series of light pulses from the LiDAR sensor. The LiDAR sensor detects return echoes of the series of light pulses, and then calculates a direct optical time-of-flight for the series of light pulses. The LiDAR sensor then determines segment lengths based on the time-of-flight of the series of light pulses. The segment lengths approximate the shape of the windrow surface along a cross-section of the windrow. The volume of a portion of the windrow may then be calculated by determining a cross-section area defined by the segments and the distance d. The volume measurement module may have a clock which generates a series of time-stamps as the collection vehicle travels through the orchard and collects data. The volume measurement module may then associate the volume calculations of the windrow with a time-stamp generated by its clock. In this way, the volume of a portion of the windrow may be calculated and fused with other collected data in real-time.

While the volume measurement module is calculating volume and as the collection vehicle travels through the rows in the orchard, the three-dimensional point-cloud scanning module may assemble three-dimensional point cloud representations of each plant in the orchard. The assembled three-dimensional point cloud may be a set of three dimensional vertices that represent the external surface of each plant in the orchard. The three-dimensional point-cloud scanning module may have a clock which generates a series of time-stamps as the collection vehicle travels through the orchard and collects data. The three-dimensional point-cloud scanning module may then associate the three-dimensional point cloud representation of each plant in the orchard with a time-stamp generated by its clock. In this way, the three-dimensional point cloud representations may be fused with other data collected in real-time.

While the volume measurement module is calculating volume, and the three-dimensional point-cloud scanning module is assembling three-dimensional point cloud representations, the inertial navigation system may calculate a geodetic position of the collection vehicle. The inertial navigation system may include an Inertial Measurement Unit ("IMU"), and a Global Positioning System ("GPS")

unit. As the inertial navigation system is transported by the collection vehicle, the inertial navigation system calculates the geodetic position of the collection vehicle in real-time based on measurements received by the GPS and the IMU. The inertial navigation system may also calculate the velocity, attitude and heading of the collection vehicle. The inertial navigation system may have a clock which generates a series of time-stamps as the collection vehicle travels through the orchard and collects data. The inertial navigation system may then associate the geodetic position data with a time-stamp generated by its clock. In this way, the geodetic position data may be fused with other collected data in real-time.

As the collection vehicle travels through the orchard the modular processing unit controls the volume measurement module, the three-dimensional point-cloud scanning module, and the inertial navigation system to collect data. The modular processing unit may receive volume measurements, geodetic positions, and three-dimensional point cloud representations and then fuses them together into a fused data set based on their associated time-stamps. The modular processing unit may then transmit the fused data set to the post-processing server.

When the post-processing server receives the fused data set from the modular processing unit, it may perform several processes that improve the accuracy of the fused data set. Specifically, the post-processing server may identify a location where the inertial navigation system provided an inaccurate geodetic position. The post-processing server may then calculate a corrected geodetic position, and update the fused data set with the corrected position of the inertial navigation system. The post-processing server may then geo-reference the different data sets transmitted by the collection vehicle. The post-processing server may geo-reference the three-dimensional point cloud representations of each plant and the plurality of volume measurements of the windrow with the updated geodetic positions. In this way, the volume measurements may be associated with a particular plant and used to determine the amount of actual yield produced by a single plant. This enables a user to then verify or confirm the amount of crop a plant was estimated to yield earlier in the growing season.

BRIEF DESCRIPTION OF THE FIGURES

The objects and features of the invention can be better understood with reference to the following detailed description and accompanying figures.

DETAILED DESCRIPTION

Embodiments of the present invention include systems, methods, and apparatuses that integrate measurements from various technologies, including LiDAR, to calculate the yield of crops in real-time and associate the yield to a specific plant or region within a grower's holdings. Yield may be calculated by scanning windrows of the crop, and estimating the volume of the windrow in a single swath of data. A comprehensive map of a grower's holdings with phenotypical, morphological, and precise geo-positional information about each plant may be generated using the systems and methods described in application Ser. No. 13/907,147, entitled "Systems and Methods for Monitoring Agricultural Products," incorporated herein by reference. The windrow volume measurements may then be combined with the comprehensive map of the grower's holdings to attribute yield to a particular plant. A grower may then associate yield measurements with other information measured by each plant. This allows growers to compare predicted yields for each plant to actual harvest data for verification, and can be used to alert growers to underperforming assets.

Figure 1:
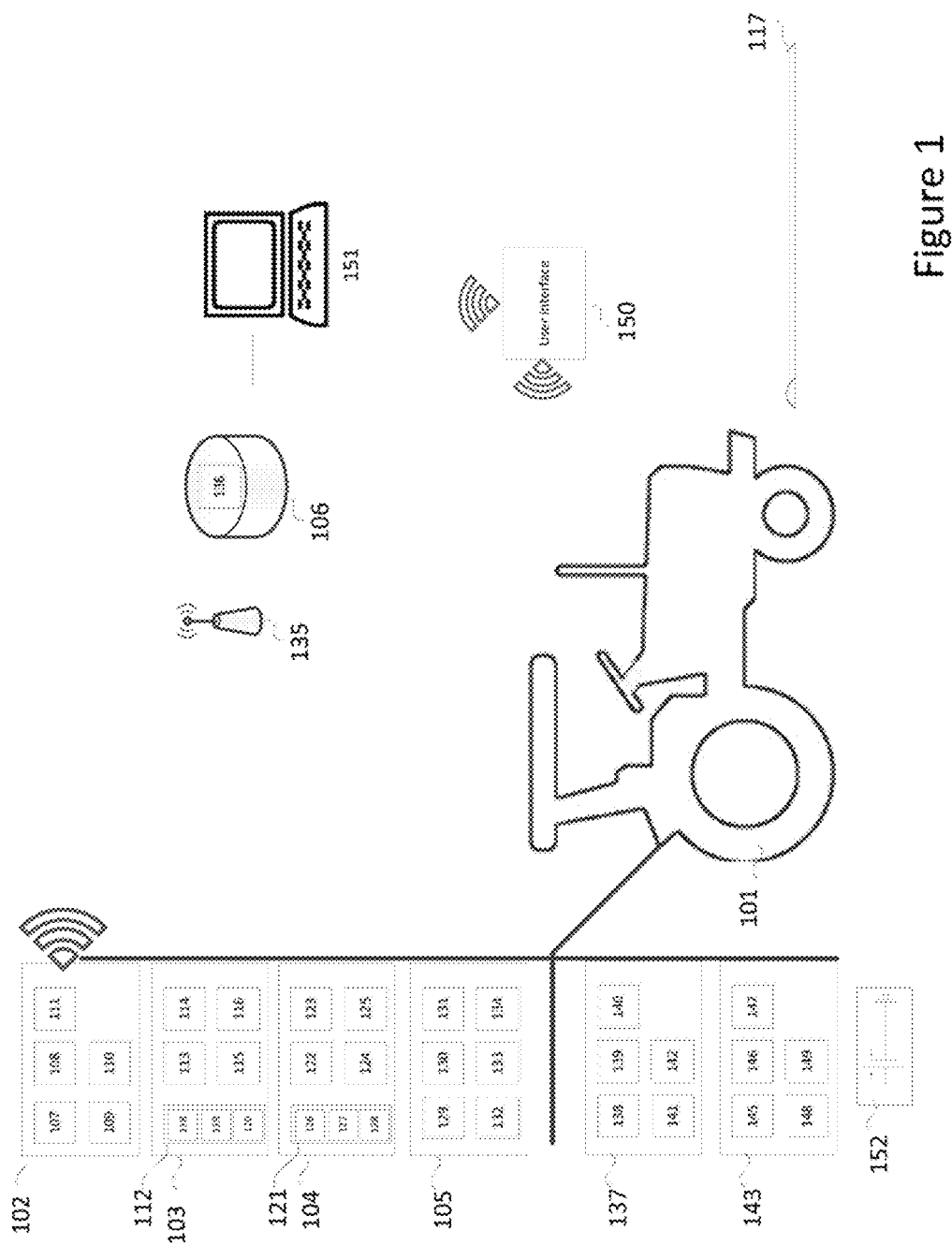
FIG. 1 shows an exemplary modular system for improved real-time yield monitoring and sensor fusion of a permanent crop in an orchard according to embodiments of the invention.

An exemplary modular system for improved real-time yield monitoring and sensor fusion is shown in FIG. 1. The system includes a collection vehicle 101, a modular processing unit 102, a volume measurement module 103, a three-dimensional point-cloud scanning module 104, an inertial navigation system 105 and a post-processing server 106. The modular system may further include one or more power sources 152 for powering the modular processing unit 102, volume measurement module 103, three-dimensional point-cloud scanning module 104, inertial navigation system 105, and other modular sensors mounted to the collection vehicle 101.

Collection vehicle 101 may be configured to transport a plurality of modular sensors through the one or more rows of one or more plants in an orchard. The collection vehicle may be a four-wheel independent suspension engine for transporting one or more modular sensors over an uneven terrain with minimal noise. The collection vehicle may have a cargo box for storing and supporting modular sensor mounts and fixtures. The cargo box may be formed with a high-density polyethylene copolymer composite material that eliminates rust, dents, and reduces noise. The collection vehicle may be, for example, a John Deere Gator™ Utility Vehicle.

Modular processing unit 102 may include a processor 107, a transceiver 108, a memory storage 109, a first clock 110, and a first communication port 111. Modular processing unit 102 may be mounted to the collection vehicle 101, by for example, affixing the modular processing unit 102 to the cargo box. The first clock 110 may be a clock generation circuit, crystal or similar device that is used to generate the clock signal at predetermined frequencies. The first clock may generate a clock signal that is provided to other components of the modular processing unit 102, such as the processor 107, memory storage 109, transceiver 108, and first communication port 111, which carry out a set of operations during one or more cycles of the clock signal. The first clock 110 also generates a series of time-stamps which as described below may be used to fuse data received from the volume measurement module 103, three-dimensional point-cloud scanning module 104, inertial navigation system 105, and other modular sensors. The first clock 110 may be synchronized to other clocks in the system. For example, the first clock 110 may be synchronized with a second clock 116 of the volume measurement module 103, such that the first clock 110 and second clock 116 may generate series of time stamps that are in sync. In this way, measurements received by the volume measurement module 103 may be fused with other data collected by the modular system. For example, the data from the volume measurement module 103 may be fused with data from an inertial navigation system 105 or a weight measurement module 137.

The volume measurement module 103 may include a first Light Detection and Ranging ("LiDAR") sensor 112, a processor 113, a memory storage 114, a second communication port 115, and a second clock 116. The volume measurement module 103 may be mounted to the collection vehicle 101 and coupled to the modular processing unit 102 by the communication ports of the modular processing unit 102 and volume measurement module 103. In some embodiments, the modular processing unit 102 and volume measurement module 103 may communicate over a CAN bus, LAN-TCP/IP cables, or serial cables. In other embodiments, the modular processing unit 102 and volume measurement module 103 may communicate wirelessly to each other.

According to some aspects of the invention, the volume measurement module 103 uses the LiDAR sensor to measure the volume of a windrow 117 formed in a row of the orchard in real-time as the collection vehicle 101 moves throughout the orchard. Specifically, as the collection vehicle drives over a windrow, the first LiDAR sensor 112 scans the ground by emitting pulses of light every distance d that the collection vehicle travels. As the collection vehicle travels over the windrow, the sensor detects the pulses of light that are reflected off the windrow. As explained below, the first LiDAR sensor 112 detects the light pulses to calculate distances and model geometric aspects of the cross-section of the windrow. This may then be used to measure a volume of a portion of the windrow. Specifically, the first LiDAR sensor 112 periodically emits a series of light pulses as a lateral scan over the windrow formed in a row of the orchard. It then detects return echoes of the plurality of light pulses, and calculates a direct optical time-of-flight of the light pulse based on the time of emission and the time the return echo is received. The first LiDAR sensor 112 then determines a plurality of segment lengths based on the time-of-flight of the series of light pulses. The segment lengths are distances measured from the first LiDAR sensor 112 to the windrow surface along a cross-section of the windrow 117. Thus, the segment lengths may approximate the shape of the windrow 117 surface along it's cross-section. As explained in more detail below, the first LiDAR sensor 112 may calculate a volume of the windrow by determining the area underneath the segment lengths and the distance d between two lateral scans.

While the first LiDAR sensor 112 is emitting and receiving pulses of light, it is also generating a series of time-stamps using the second clock 116. Thus, the volume measurement module 103 may associate the measured volume of the windrow cross-section with a time-stamp generated by the second clock 116. The time-stamps may then be used to fuse the volume measurements with data calculated by other components in the system, such as for example, the three-dimensional point-cloud scanning module 104, the inertial navigation system 105, the weight measurement volume module 137 or other modular sensors.

The second clock 116 may be a clock generation circuit such as the first clock 110, and generate a series of time-stamps. As the volume measurement module 103 measures the volume of the orchard, the volume measurement module uses the second clock 116 to generate time-stamps that are associated with the volume of a windrow cross-section. Each volume measurement calculated by the volume measurement module 103 may thus be associated with a time-stamp generated by the second clock 116.

In some embodiments of the invention, the first LiDAR sensor 112 may include a light source 118 for periodically emitting pulses of light, a photo-detector 119 for collecting echoes of the emitted pulses of light and a signal processor 120 for processing the collected echoes. The signal processor 120 can measure and calculate various properties of the object that a pulse emission reflected off of, such as for example, distance. In some embodiments of the invention, the light source 118 may be an LED light, and the LiDAR sensor 112 may be for example, a Leddar™ M16 Module.

The three-dimensional point-cloud scanning module 104 may include a second LiDAR sensor 121, a processor 122, a memory storage 123, a third communication port 124, and a third clock 125. The three-dimensional point-cloud scanning module 104 may be mounted to the collection vehicle 101 and coupled to the modular processing unit 102 by the communication ports of the modular processing unit 102 and three-dimensional point-cloud scanning module 104, in the same manner as described with respect to the volume measurement module 103.

As explained below, the three-dimensional point-cloud scanning module 104 uses the second LiDAR sensor 121 to generate a point cloud representation of the orchard in real-time as the collection vehicle 101 moves throughout the orchard. Specifically, as the collection vehicle drives through an orchard row, the second LiDAR sensor 121 continuously rotates around its central axis to scan across a wide-angled field of view by emitting pulses of light. As the collection vehicle 101 travels through an orchard row, the second LiDAR sensor 121 detects any pulses of light that are reflected off the surface of an object in the sensor's field of view. While the second LiDAR sensor 121 is emitting and receiving pulses of light, it is also generating a series of time-stamps using the third clock 125. As explained below, the second LiDAR sensor 121 detects the light pulses to assemble a three-dimensional point cloud that represents each plant in the orchard. The three-dimensional point-cloud scanning module 104 may then associate the three-dimensional point cloud representation of each plant in the orchard with a time-stamp generated by the third clock 125.

The third clock 125 may be a clock generation circuit such as the first clock 110, and generate a series of time-stamps. As the three-dimensional point-cloud scanning module assembles point clouds of plants in the orchard, the three-dimensional point-cloud scanning module 104 uses the third clock 125 to generate time-stamps that are associated with each three-dimensional point cloud. Each three-dimensional point-cloud calculated by the three-dimensional point-cloud scanning module 104 may thus be associated with a time-stamp generated by the third clock 125.

The second LiDAR sensor 121 may include a light source 126 for periodically emitting pulses of light, a photodetector 127 for collecting echoes of the emitted pulses of light and a signal processor 128 for processing the collected echoes. In some embodiments, the light source 126 may be a laser diode, and the second LiDAR sensor 121 may be a survey-grade LiDAR sensor, such as for example, a RIEGL™ VUX-1 laser scanner. The signal processor 128 can measure and calculate various properties of the object that was hit by the light pulse, such as for example, distance to the second LiDAR sensor 121. The signal processor 128 may create a set of three-dimensional vertices that correlate to the measurements and calculations of the reflected light pulses. The vertices may be defined by X, Y, and Z coordinates. The set of vertices may then be assembled together into a point cloud. In a point cloud, the individual vertices approximate the surface the object that was in the second LiDAR sensor's 121 field of view. Because the second LiDAR sensor 121 may generate high density point clouds, the three-dimensional point cloud may simulate the object's surface at a very high level of detail and resolution. For example, the three-dimensional point cloud may simulate individual leaves, branches, or fruit of a plant.

In some embodiments, the second LiDAR sensor 121 utilizes waveform LiDAR, and in yet other embodiments discrete LiDAR is utilized. According to some embodiments of the invention that utilize discrete LiDAR, when the light source 126 emits a laser pulse, the laser pulse will typically reflect off an object in the environment, and return to a light-detecting sensor 127. Several measurements may be taken on a single pulse returned to the light-detecting sensor, such as for example, the range to the object, the sensor time, the angle relative to the sensor, and the intensity of the returned pulse. The sensor time corresponds to the precise time the measurement was taken and received and, as discussed below, may be used to geo-reference measurements taken by the sensor. Specifically, the sensor time is the time a recorded echo is received at a receiver. The position of the sensor is also correlated to the sensor time, allowing the measurements to be related to the sensor position. In some embodiments of the invention, a second pulse is primed and emitted at a specific interval after the first pulse has been emitted. Discrete LiDAR sensors may also record multiple returns from a single emitted pulse, indicating that the pulse reflected off multiple surfaces.

According to some embodiments of the invention that utilize waveform LiDAR, the returned laser pulse may be separated into three dimensions: reflection; intensity; and pulse width. The extracted waveform may be fitted to a smoothed pulse waveform using a Gaussian filtering process, which provides a continuous measured signal. Whereas discrete LiDAR provides a sample of range data points, waveform LiDAR may provide information at each point along the surface of an entire object. Because waveform LiDAR produces a continuous signal, it enables a higher degree of accuracy and details, and thus, provides more detailed measurements than discrete LiDAR. Specifically, the reflectance, intensity and pulse width of waveform LiDAR yields higher point density measurements, and captures the intricacies and details of foliage, fruit, blossoms, and other similar growths that grow on plants.

Further, waveform LiDAR is capable of measuring reflectance of a returned laser pulse which enables the system to isolate physical attributes of a plant. The signal measured at the light-detecting sensor is converted to a digital signal, to produce an amplitude reading and obtain a measurement of the echo width defining the vertical distribution of a target's surface as well the surface roughness of the target in question. The amplitude reading from the recorded waveform may then be compared to the emitted waveform and normalized accordingly. The normalized amplitude reading may then be calibrated to yield reflectance. The reflectance value associated with a particular amplitude reading is determined by utilizing a lookup table that correlates range-dependent amplitude readings with reflectance. In some embodiments, the waveform LiDAR sensor may perform full waveform calculations on-board and in real-time as the collection vehicle travels through the orchard. In a preferred embodiment of the invention, the second LiDAR sensor is configured to generate between 300,000 and 800,000 points per second, which may capture details of plants with varying densities and coverages. In preferred embodiments, the second LiDAR sensor is configured to generate 550,000 points per second.

The inertial navigation system 105 calculates a geodetic position of the collection vehicle 101 and may include an Inertial Measurement Unit ("IMU") 129, a Global Positioning System ("GPS") 130, a processor 131, a memory storage 132, a fourth clock 133, and a fourth communication port 134. The inertial navigation system 105 may be mounted to the collection vehicle 104 and coupled to the modular processing unit 102 by the communication ports of the modular processing unit 102 and inertial navigation system 105 in a similar manner as the volume measurement module described above.

As explained below, while the collection vehicle 101 travels over the rows of the orchard, the inertial navigation system 105 uses the IMU 129 and GPS 130 to calculate the geodetic position of the collection vehicle. While the inertial navigation system is calculating geodetic positional data, it is also generating a series of times-stamps using the fourth clock 133. The time-stamps may then be used to fuse the geodetic positions of the collection vehicle 101 with data calculated by other sensors, such as for example the three-dimensional point-cloud scanning module 104 or volume measurement module 103.

According to some embodiments of the invention, the inertial navigation system 105 may calculate the geodetic position of the collection vehicle 101 in real-time based on measurements received by the GPS 130 and the IMU 129. Based on these measurements, the inertial navigation system 105 may calculate a velocity of the collection vehicle. The IMU 129 may include one or more accelerometers, gyroscopes, and magnetometers for providing relative measurements of motion and orientation. Thus, the IMU 129 may calculate an attitude and heading of the inertial navigation system 105.

The fourth clock 133 may be a clock generation circuit such as the first clock 116, and generate a series of time-stamps. As the inertial navigation system 105 calculates geodetic positions of the collection vehicle 101, the inertial navigation system 105 uses the fourth clock 133 to generate time-stamps that are associated with the geodetic position of the collection vehicle 101. Each geodetic position calculated by the inertial navigation system 105 may thus be associated with a time-stamp generated by the fourth clock 133.

The post-processing server 106 may include a receiver 135 and a processor 136 that receives transmissions from the modular processing unit 102. According to some embodiments of the invention, the modular processing unit 102 is configured to control the volume measurement module 103, the three-dimensional point-cloud scanning module 104, and the inertial navigation system 105. For example, the modular processing unit 102 may use the communication ports to control when to begin measuring volume, generating three-dimensional point clouds, calculating geodetic positions, or collecting and calculating data from other modular sensors described below. When the collection begins, the modular processing unit 102 then receives the volume measurements, three-dimensional point clouds, and geodetic position measurements and their associated time-stamps. The modular processing unit 102 may also use the communication ports to synchronize the clocks of the volume measurement module 103, the three-dimensional point-cloud scanning module 104, the inertial navigation system 105, and other modular sensors and components described below.

In some aspects of the invention, the modular processing unit 102 may fuse the volume measurements, geodetic positions calculations, and three-dimensional point cloud representations together into a fused data set. Specifically, the modular processing unit 102 may align time-stamps generated from each sensor and cross-correlate the different data sets with each other using their time-stamps. For example, the modular processing unit 102 may identify the volume measurement taken at time-stamp $t_1$ as $v_1$, the three-dimensional point cloud generated at time-stamp $t_1$ as $c_1$, and the geodetic position data that was measured at time-stamp $t_1$ as $p_1$. The modular processing unit 102 may then associate $v_1$, $c_1$, and $p_1$ with $t_1$ in a data structure as a fused data set. In some aspects of the invention, the modular processing unit may fuse $v_1$, $c_1$, and $p_1$ with $t_1$ in real-time as the collection vehicle 101 travels through the orchard.

The modular processing unit 102 may transmit the fused data set to the post-processing server 106. In some embodiments of the invention, the transceiver 108 of the modular processing unit is used to wirelessly transmit the fused data set to the post-processing server 106 in real-time as the collection vehicle travels through the orchard. As discussed below, a user may select an input button on a user interface 150 that initiates the transmission of the fused data set from the modular processing unit 102 to the post-processing server 106.

According to some aspects of the invention, the post-processing server 106 receives the fused data set from the modular processing unit 102 and performs one or more routines that eliminate errors, reduce noise, and improve accuracy in the fused data. For example, the post-processing server 106 may process the geodetic position data collected by the inertial navigation system 105 to identify any locations where the inertial navigation system 105 provided an inaccurate geodetic position. For example, if the collection vehicle 101 was underneath the canopy of a plant thus obstructing the inertial navigation system 105 from receiving GPS signals at its receiver, the GPS data would become inaccurate and shift or jump from what was otherwise a relatively smooth positional trajectory. The post-processing server 106 may identify variances in the positional trajectory data using statistical error detection algorithms and processes.

When an error is detected in the geodetic position data, the post-processing server 106 calculates a corrected geodetic position based on other data collected by the inertial navigation system 105. For example, the post-processing server 106 may use data collected by the IMU 129 to determine the corrected position of the collection vehicle 101 while its signal reception was obstructed by a plant canopy. The geodetic position data may then be updated with the corrected position of the inertial navigation system 105. The fused data set may then be updated by replacing the inaccurate geodetic position with the updated geodetic position.

In some embodiments of the invention, after the post-processing server 106 determines that there was an error in the GPS data (e.g., because of a canopy obstructing the signal to a GPS satellite), the post-processing server 106 compares the GPS data to the IMU data (which may include roll, pitch, or yaw data, or any combination thereof). For example, if the GPS data suggests that the trajectory of the collection vehicle shifted in one direction, yet the IMU data suggests the trajectory of the collection vehicle did not change based on its measured yaw, the post-processing server 106 may modify the position data to reflect the readings of the IMU 129. The post-processing server 106 may then determine that the GPS data is inaccurate based on the comparison. The post-processing server may then generate a Smooth Best Estimate Trajectory ("SBET"), which is described in more detail below.

In some embodiments of the invention, the GPS unit 130 of the inertial navigation system 105 may include a second IMU integrated into the circuitry of the GPS unit. The second IMU may then be used to correct the GPS calculations in the same manner as described above, and in real-time. As explained above, the second IMU may measure physical movements of the device in at least 3 axes, including pitch, yaw, and roll. The yaw axis measurement may be used to compensate for GPS signal outages or position errors. When traveling down a substantially straight trajectory, such as for example when traveling through a row, the inertial navigation system 105 may use the yaw axis measurement data to project the path of the collection vehicle 101 along the same substantially straight trajectory it was previously traveling on. In this way, the IMU data is used to smooth the position outliers by assuming the collection vehicle continued to travel along the same substantially straight trajectory it was previously traveling on. In other embodiments of the invention, different trajectories may be modeled using information known about the orchard or the route or path the collection vehicle was planned to take. For example, knowledge of the layout of the orchard may include the geometry of the rows formed in the orchard. The layout of the circular or spiraled rows, may then be used to model circular or spiraled trajectories of the collection vehicle. Similarly, knowledge of what path the collection vehicle is planned to take in an orchard may be used to extrapolate the collection vehicle's trajectory path.

In other embodiments of the invention, the inertial navigation system 105 further comprises a base receiver station positioned in a fixed location proximal to the orchard. While the inertial navigation system 105 travels through the orchard, the inertial navigation system may receive messages from a GPS satellite which it may forward to the base station. In this way, the inertial navigation system 105 functions similarly to a rover station in a real-time kinematic positioning system. While the inertial navigation system 105 transmits messages to the base station, the base station in parallel receives the same messages from the GPS satellite. Thus, the base station receives messages from the GPS satellite in sync with the inertial navigation system. The base station may then compare the GPS message received directly from the GPS satellite to the GPS message received from the inertial navigation system 105. Based on this comparison, the base station may determine whether the collection vehicle 101 has deviated from a trajectory path based on its GPS data, and thus if there have been any anomalies or errors with the inertial navigation system 105. The messages the base station receives from the GPS satellite describe the orbital information (ephemeris) of the satellites in view and the pseudo-range data (observables or epochs) describing the position of the other satellites in the Global Navigation Satellite System ("GNSS") with respect to the position of the base station. The base station will reliably know the geometry of the satellites because it will have a constant viewing point to them. As such, it is enabled to provide reliable position corrections to the rover when the rover has an outage or cycle slip.

In some embodiments of the invention, the post-processing server 106 uses the orbits or position of the satellites to improve the accuracy of the data. Specifically, the post-processing server 106 may download precise ephemeris files which describe the exact orbit and position information of the satellites. The exact orbit and position information may then give precise position measurements, improving positional accuracies by as much as a few centimeters. As described below, having high accuracy at the resolution of centimeters enables the modular system to incorporate sprayers that targets plants or plant regions with a high degree of precision and accuracy, such as for example, specific trunks or tree branches. In this way, the post-processing server 106 may correct errors that occur during real-time collection, eliminate bias from poor satellite coverage, and gain access to more precise orbital information.

In some embodiments of the invention, when the base station determines that there has been a deviation, the base station may then compare the GPS data of the collection vehicle 101 to the GPS data received directly from the GPS satellite. If the GPS data received directly from the GPS satellite suggests a different trajectory path, the post-processing server 106 may determine that the GPS data of the inertial navigation system is inaccurate. The post-processing server may then generate a SBET, described in more detail below.

In some embodiments of the invention, the post-processing server 106 may use a weighting system for the positional data sources when generating the SBET. Specifically, if one positional data source is consistently unreliable, the post-processing server 106 may give that positional data source less weight when creating a SBET. For example, one GPS satellite may be causing a bias to the positional data. Knowing that the particular GPS satellite is causing a bias, the post-processing server 106 may correct for that bias by according that satellite less weight when calculating a geodetic position.

A SBET may be created by performing a series of filtering algorithms on the geodetic positional data calculated by the inertial navigation system 105. For example, in some embodiments of the invention, the post-processing server 106 may apply a Kalman filter to the geodetic positional data measured by the inertial navigation system 105. It may then continue to filter the geodetic positional data by applying a forward, reverse, combine, precise forward, and then smoothing correction filter to the geodetic positional data, resulting in a SBET. Whereas the original/raw geodetic positional data may be accurate to about 10 meters during a collection, in some aspects of the invention, the improved error identification and correction processes described above allow the inertial navigation system 105 to achieve a resolution of geodetic position data as low as 1-3 centimeters in both the horizontal and vertical axes, and as low as millimeters in the horizontal axis.

In some embodiments of the invention, the modular processing unit 102 or post-processing server 106 may be used to translate the measurements of the volume measurement module 103 and three-dimensional point cloud scanning module 104 from one coordinate system to another. The sensors of the volume measurement module 103 and three-dimensional point cloud scanning module 104 may collect data in a Scanner Own Coordinate System ("SOCS"). The SOCS is a coordinate system that uses the sensor as the reference frame, and all measurements collected by the sensor are in relation to that sensor's reference frame. For example, when the three-dimensional point cloud scanning module 104 generates a point cloud, the coordinates of each vertice in the point cloud are based on the second LiDAR sensor's SOCS. In order to translate the measurements from the second LiDAR sensor's SOCS to real-world geodetic coordinates, the post-processing server 106 or modular processing unit 102 uses the inertial navigation system 105 positional data. Specifically, the modular processing unit 102 or post-processing server 106 may use the IMU measurements to translate the SOCS coordinates to geodetic coordinates. For example, the modular processing unit 102 may apply a rotational matrix to the SOCS measurements to translate them into the IMU's reference frame. The rotational matrix may be a 3×3 matrix for rotational and X-Y-Z translation that maps a SOCS coordinate to the IMU's reference frame. The modular processing unit 102 or post-processing server 106 may then use the time-stamps of the inertial navigation system 105 to correlate the SOCS coordinates of the sensors with real-world geodetic positions. In this way, the modular processing unit or post-processing server may translate the SOCS of the sensor measurements into the reference frame of the inertial navigation system.

According to some embodiments of the invention, the volume measurements and the three-dimensional point cloud representations of each plant may then be geo-referenced with the updated geodetic positions. For example, each vertice of the three-dimensional point cloud may be associated with a geodetic position. Thus, the three-dimensional point clouds may be mapped onto a geodetic coordinate system and rendered using mapping interfaces described below. Similarly, the volume cross-sections of the windrows may be mapped onto a geodetic coordinate system, and also may be rendered using a mapping interface as described below. Measurements and data from the weight measurement module and other modular sensors may likewise be mapped onto a geodetic coordinate system, and also may be rendered using a mapping interface as described below.

In one aspect of the invention, the modular system may geo-reference the high-resolution positional data described above with the high-resolution point-cloud data to create a high-resolution, accurate and detailed three-dimensional representation of an orchard. Specifically, the three-dimensional point cloud simulates the surface of the plants in the orchard. Because the three-dimensional point cloud scanning module 104 can generate up to billions of vertices for a single plant, the three-dimensional point cloud can accurately depict the precise contour of each plant's surface at a high level of detail.

Figure 11:
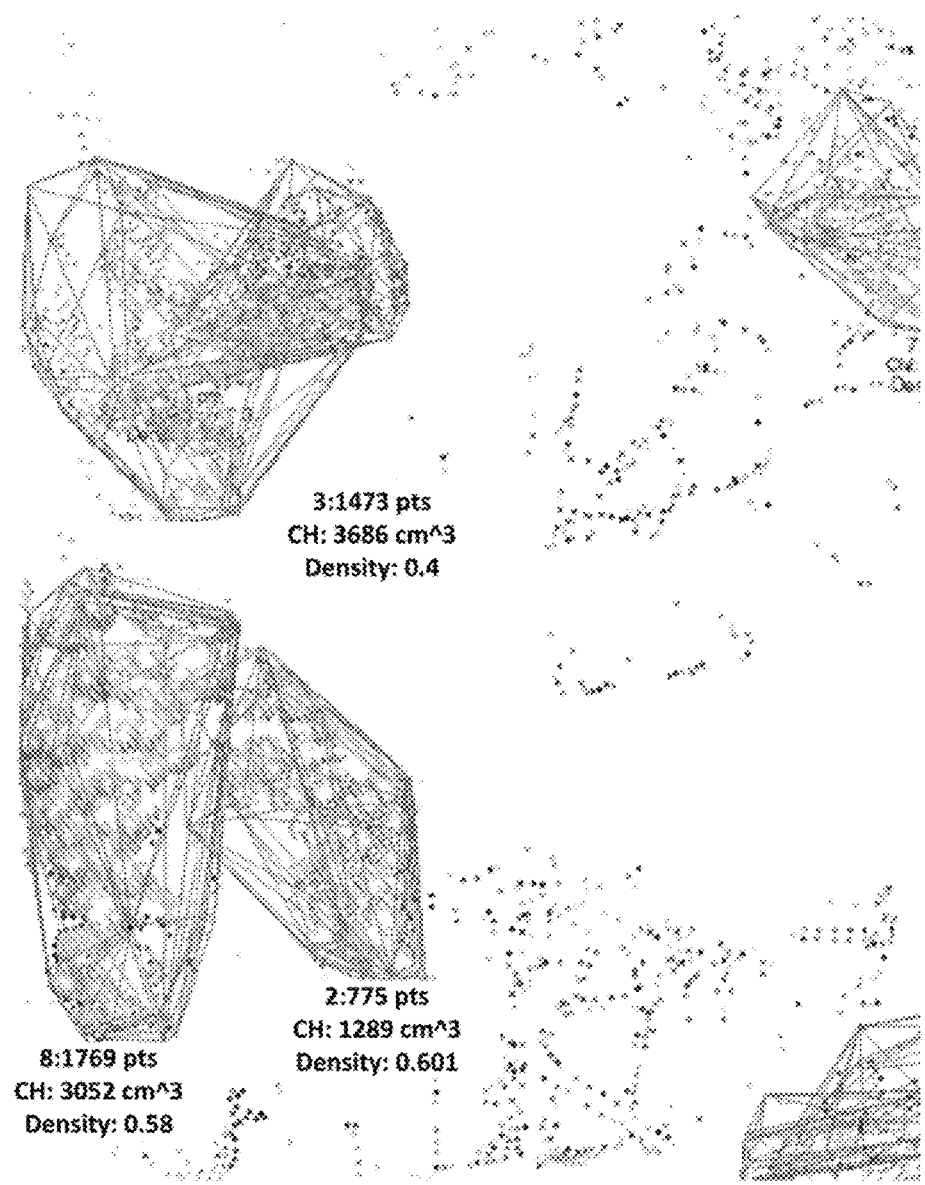
FIG. 11 shows an exemplary embodiment of a three-dimensional point cloud of a grape vine having sets of vertices clustered according to embodiments of the invention.

When the three-dimensional point cloud representations are geo-referenced with the high-resolution and high-accuracy geodetic positional data, the three-dimensional representation of the plant may be mapped into a real-world coordinate system, enabling analysis with other geospatial data sets at a high level of accuracy and detail that was previously unattainable. For example, as explained below, the three-dimensional point cloud representation may be rendered in a map that displays a plant three-dimensionally and in a spatial context that enables detailed analyses of the plants. Specifically, the geo-referenced data may enable a user to measure and calculate morphological attributes of the plant. For example, a user may measure and calculate the diameter of a plant using the distances between the vertices in the point cloud. As another example, FIG. 11 shows a three-dimensional point cloud representation of a grape vine. The highly detailed level of resolution enables the system to not only identify clusters of the plant's fruits, blossoms, branches, or leaves, but also calculate and analyze their size, and related morphological traits.

Figure 9:
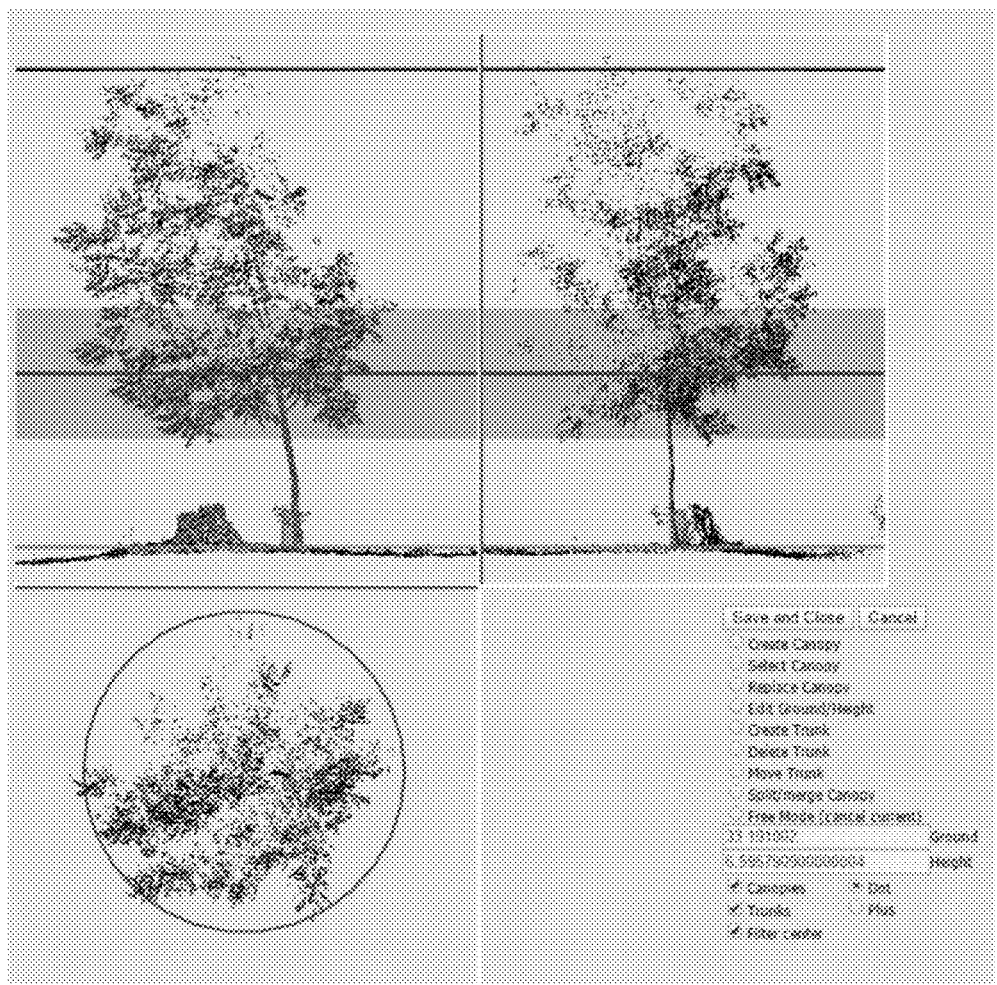
FIG. 9 shows a user interface for analyzing post-processing server data according to embodiments of the invention.

In some embodiments of the invention, the post-processing server 106 may provide a user interface for a user to open, view, and analyze the fused data to calculate, modify, manipulate, and store various attributes of the plant. For example, as shown in FIG. 9, a user may view a three-dimensional point cloud of a plant. As FIG. 9 shows, the user interface may allow a user to visually inspect the three-dimensional point cloud and calculate attributes such as canopy height, canopy diameter, canopy density, trunk width. The user interface may also allow the user to input geodetic positional data of the plant, such as its centroid. The post-processing server 106 will then store the attribute calculations with the fused data set of the plant for later viewing and analysis. In other embodiments of the invention, the post-processing server 106 may automatically calculate morphological attributes of the plant. The post-processing server 106 may, for example, cluster the vertices or create polygon mesh models derived from point clouds, from which plant height, trunk diameter, canopy diameter, and canopy density may be measured. For example, FIG. 11 shows an embodiment of a three-dimensional point cloud of a grape vine having sets of vertices grouped into their clusters. As FIG. 11 shows, the post-processing server may calculate the size and other dimensions of the cluster using the geo-referenced positional data of the vertices. The user may then verify the accuracy of the automatic calculations using the interface shown in FIG. 9, and if there is an error, provide a corrected calculation. In this way, the post-processing server 106 allows operators to provide QA/QC and enhance the quality of the fused data set that is received and delivered to a customer portal.

In some embodiments of the invention, the post-processing server 106 may perform morphological analyses of the fused data using various segmentation and classification algorithms. For example, when analyzing the three-dimensional representation of a tree, the modular system may begin by searching for boundary of the three-dimensional point-cloud or other sensor data. In some embodiments, the boundaries are identified by analyzing a change between two data point values. Algorithms that determine similarity and rate of change from data point to data point using features such as color, pattern, or distance may be used to classify points as belonging to specific objects. A change of more than a threshold amount may represent an edge condition, which signifies the end of an object, or the beginning of another. These edges mark boundaries that can be used to classify each of the objects in an image or point cloud. After finding a boundary, the post-processing server may attempt to identify a canopy, and then a trunk. The modular system may identify a canopy by looking for a boundary or edge condition within a specific height range. To automatically extract a trunk, the post-processing server may attempt to identify a series of arcs in the three-dimensional point-cloud. The post-processing server 106 may then attempt to fit the three-dimensional point-cloud into a cylindrical shape. The portion of the point cloud having a best cylindrical fit may be identified as the plant trunk. The post-processing server may then extrapolate plant trunk height. The post-processing server may use similar processes to identify branch structure, trunk segments, biomass, tree stand structure, canopy height, extent, fruit clusters, and similar dimensional and structural plant features.

The attributes described above may be used to determine the health and yield potential of individual trees and complete horticultural systems. Similarly, these attributes may also be used to determine genome, vitality, risk of damage from wind, access to sunlight, and whether a plant has sufficient resources for photosynthesis.

In some aspects of the invention, the geo-referenced data may enable further spatial analysis of the orchard by allowing the user to overlay other data sets onto the three-dimensional point cloud representations. For example, modular sensors may collect photographic or spectral data as described in more detail below. The data collected by these sensors may be associated with time-stamps and geo-referenced in the same manner as described above. In this way, the photographic and spectral data may also be associated to a plant having a three-dimensional point cloud representation. Thus, each vertice or a group of vertices in a three-dimensional point cloud may be associated with other data from other sensors. For example, a user may view the three-dimensional point cloud representation of a leaf in conjunction with the spectral data for that leaf.

In some embodiments of the invention, the modular system may further include a weight measurement module 137 that measures the weight of a portion of a windrow formed in a row of the orchard. The weight measurement module 137 may include a load cell sensor 138, a processor 139, a memory storage 140, a fifth communication port 141, and a fifth clock 142. The weight measurement module 137 may be coupled to the collection vehicle 101 and coupled to the modular processing unit 102 by the communication ports of the modular processing unit 102 and weight measurement module 137 in a similar manner as described above with respect to the volume measurement module 103. The load cell sensors 138 are mobile scales that may be mounted onto the collection vehicle 101 and measure the weight of the crop as they are transferred from the windrow 117 onto the collection vehicle 101.

According to some aspects of the invention, the weight measurement module 137 uses the load cell sensors 138 to measure the weight of a windrow portion formed in a row of the orchard in real-time as the collection vehicle 101 moves throughout the orchard. Specifically, as the crop is transferred to the collection vehicle 101, the load sensors record the added weight detected by the load cell sensor 138.

The fifth clock 142 may be a clock generation circuit such as the first clock 116, and generate a series of time-stamps. As the weight measurement module 137 measures the weight of a portion of the windrow volume, the weight measurement module 137 uses the fifth clock 142 to generate time-stamps that are associated with the windrow portion that was weighed by the load cell sensor 138. Each weight measurement calculated by the weight measurement module 137 may thus be associated with a time-stamp generated by the fifth clock 142.

The modular processing unit 102 may be configured to control the weight measurement module 137 in a similar manner as with respect to the volume measurement module 103. For example, the modular processing unit 102 may control when the weight measurement module begins to collect weight measurements. When the collection begins, the modular processing unit 102 receives weight measurements from the weight measuring module 137 and the associated time-stamps. The modular processing unit 102 then fuses the volume measurements, the geodetic positions, the three-dimensional point cloud representations, and the weight measurements together into a fused data set. The fusion is based on the associated time-stamps, as described above.

In some embodiments of the invention, the modular processing unit 102 uses the volume cross-sections of the windrow to determine how much crop to sweep into a weight measurement module 137 at once. In this way, the fusion of volume data with weight data is highly cross-correlated and accurate.

The fused data containing weight measurement data may then be transmitted to a post-processing server 106 as discussed above. The post-processing server 106 may then update the geodetic position data and geo-reference the weight measurements with updated position data as described above.

In some embodiments of the invention, the modular system may further include one or more crop-specific measurement modules 143. The crop-specific measurement module 143 may include sensors 145 that are tailored for measuring specific attributes unique to the crop, a processor 146, a memory storage 147, a communication port 148, and a sixth clock 149. For example, a crop-specific measurement module 143 for an orange grove may include a spectral sensor, a thermal sensor, and a temperature sensor that collects spectral imagery, thermal imagery, and temperatures over specific ranges unique to oranges.

The crop-specific measurement module 143 may be coupled to the collection vehicle 101 and coupled to the modular processing unit 102 by the communication ports of the modular processing unit 102 and crop-specific measurement module 137 in a similar manner as described above with respect to the volume measurement module 103. The sixth clock 149 may be a clock generation circuit such as the first clock 116, and generate a series of time-stamps. As the crop-specific measurement module 143 collects data from its sensors, the crop-specific measurement module 143 uses the sixth clock 149 to generate time-stamps that are associated with the data collected by the sensors 145 at that time. Each measurement calculated by the crop-specific measurement module 143 may thus be associated with a time-stamp generated by the sixth clock 149.

The modular processing unit 102 may be configured to control the crop-specific measurement module 143 in a similar manner as with respect to the volume measurement module 103. For example, the modular processing unit 102 may control when the crop-specific measurement module 143 begins to collect measurements. When the collection begins, the modular processing unit 102 receives measurements from the crop-specific measurement module 143 and the associated time-stamps. The modular processing unit 102 then fuses the measurements, the geodetic positions, the three-dimensional point cloud representations, the volume measurement data, and the weight measurements together into a fused data set. The fusion is based on the associated time-stamps, as described above. The crop-specific measurements may then be geo-referenced at the post-processing server for further analysis.

In some embodiments of the invention, the sensors 145 may include RGB, thermal, multispectral, hyperspectral, thermal, infrared, radar, ultrasonic, x-ray sensors, or any combination thereof. The sensors 145 may be accompanied by corresponding clocks that function as the first clock 116 described above, and generate a series of time-stamps. As the sensors collect data of the windrow or the orchard, the sensor clocks generate time-stamps that are associated with the location that the sensor collected the data. Each measurement calculated by the sensor may thus be associated with a time-stamp generated by the sensor clock. Similar to the volume measurement and weight measurement modules described above, the modular processing unit may be configured to control the sensors. For example, the modular processing unit may control when the sensors begin to collect measurements. When the collection begins, the modular processing unit receives measurements from the sensor and the associated time-stamps. The modular processing unit then fuses the sensor measurements, the geodetic positions, and the three-dimensional point cloud representations into a fused data set. The fusion is based on the associated time-stamps, as described above. The fused data containing additional sensor data may then be transmitted to a post-processing server as discussed above. The post-processing server may then update the geodetic position data and geo-reference the sensor measurements with updated position data as described above.

In some embodiments of the invention, the post-processing server 106 associates the volume measurements described above to a plant in an orchard. For each windrow volume measurement collected by the volume measurement module 103, the post-processing server 106 determines which plant was closest in proximity based on the geo-referenced volume measurement data and the geo-referenced three-dimensional point cloud representation. The post-processing server 106 may then aggregate all the volume measurements associated with a single plant, indicating the total volume of crop produced by the plant. The post-processing server 106 may then calculate the total yield for an orchard by aggregating the yield measurements for each plant. Whereas some yield monitoring systems may only provide end-of-day yield measurements that correspond to an entire orchard, the modular system may determine the actual yield at the level of granularity of the plant, or a section of a plant.

Similarly, the post-processing server 106 may associate the weight measurements described above to a plant in an orchard. For each windrow weight measurement collected by the weight measurement module 137, the post-processing server determines which plant was closest in proximity based on the geo-referenced weight measurement data and the geo-referenced three-dimensional point cloud representation. The post-processing server 106 may then aggregate all the weight measurements associated with a single plant, indicating the total weight of crop produced by the plant. The post-processing server 106 may then calculate the total yield for an orchard by aggregating the yield measurements for each plant.

In some aspects of the inventions, the post-processing server 106 may use the weight or volume measurements to generate a report card that confirms or verifies crop yield estimates calculated earlier in the year. A crop yield estimate may be calculated for each plant in the orchard based in part of three-dimensional point cloud data. For example, the post-processing server 106 may analyze the three-dimensional point cloud data to determine, among other things, the number of fruits or nuts growing on the tree. At the end of the season, when the fruits or nuts are collected into a windrow, the modular system may collect volume and weight measurements as discussed above. These actual volume and weight measurements may then be compared to the estimate to determine how accurate the earlier estimation was. In this way, the modular system may provide a report card that confirms or verifies the accuracy of the initial crop yield estimates.

In another aspect of the invention, the volume measurements may be used to validate or calibrate the sensors of the weight measurement module 137, and vice versa. Over time, sensors, such as load cell sensors 138, lose accuracy, and farmers may not calibrate the sensors as often as they should. The modular system may be used to recalibrate the load cell sensors 138 in an efficient and streamlined manner. Specifically, the collection vehicle 101 may first offload the crop that was collected during a swath into a weighing station. The weighing station may be a fully calibrated, highly accurate scale. The total weight of the crop measured at the weighing station should correlate to the measurements of the load cells logged during the swath. If the measurements of the load cell sensors do not correlate to the weighing station, the load cells may need re-calibrating.

The modular system may be calibrated using the user interface 150 described below. The system may be calibrated by affixing the volume measurement module 103, the three-dimensional point-cloud scanning module 104, the weight measurement module 1037, and any crop-specific measurement module 143 or additional sensors to the collection vehicle 101. These modules and sensors may be mounted to the collection vehicle at a fixed height above ground. A user may then enter an input to the user interface indicating it will drive the collection vehicle to calibrate the modular system. The user may then drive the collection vehicle 101 over a predetermined stretch of road that preferably has a similar ground surface as the orchard and is at least 150 yards long. The stretch of road should be empty, having no debris or crop. After driving over the portion of road, the user may select an input on the user interface 150 indicating the calibration process has been completed. If the system has been successfully calibrated, the user interface may toggle to another screen where the user may begin collecting data. In some embodiments of the invention, the user may be required to input a manger code before performing this operation and selecting these inputs.

In some aspects of the invention, the post-processing server 106 may implement machine learning algorithms to identify patterns and associations between the estimated crop yields and the measured data, which may be, for example, the volume data, weight data, or both. The estimated plant yield may be compared with the total yield based on the aggregate windrow volume and the total yield based on the aggregate windrow weight as discussed above. The post-processing server 106 may then determine the differential between the estimated plant yield and the total yield based on the aggregate windrow volume and the aggregate windrow weight. The post-processing server 106 may then create a correlation between estimated plant yield and actual plant yield based on the differential.

The post-processing server 106 may create a set of statistical weights based on the correlation between estimated plant yield and actual plant yield using the differential discussed above. The post-processing server 106 may then create a new plant yield estimate in the same manner as described above, where for each three-dimensional point cloud representation of a plant in the orchard, a new plant yield is estimated. The post-processing server may then apply the set of statistical weights to the new plant yield estimate. The next year, the verification process may repeat itself and new statistical weights may be generated based on new volume and weight calculations. This process may continue to repeat itself each growing season; with each growing season, the estimation process will become more accurate, and the margin of error of the estimations will decrease.

In some embodiments of the invention, the modular system may further include a variable rate fertilizer dispenser mounted to the collection vehicle and coupled to the modular processing unit 102. The variable rate fertilizer dispenser may dispense fertilizer at rate that dynamically varies according to a variable rate fertilizer map and the geodetic position of the collection vehicle determined by the inertial navigation system 105. For example, the variable rate fertilizer map may provide instructions to spray one plant with more fertilizer than the other plants in the orchard. It may do this by associating a higher dosage of fertilizer with the geodetic position of the plant needing more treatment. In some aspects of the invention, the high degree of resolution and accuracy provided by the three-dimensional point cloud data and geodetic position data enable the variable rate fertilizer maps to target an individual plant or even a specific region on the plant to treat with a specific dosage of fertilizer. As the collection vehicle 101 travels through the orchard, the variable rate fertilizer dispenser may spray the individual plant, or specific region on the plant, with the dosage of fertilizer specified in the variable rate fertilizer map.

In some embodiments of the invention, the post-processing server 106 generates an updated variable rate fertilizer map based on the total yield measurements described above. For example, the post-processing server 106 may use the aggregate windrow volume and the aggregate windrow weight measurements described above to determine that a specific plant or specific region of a plant has yielded a low amount of crop. The post-processing server may be configured to determine that a yield below a predetermined threshold is classified as underperforming. The post-processing server may then update the variable rate fertilizer map to increase the amount of fertilizer applied to the underperforming plant. As the collection vehicle travels through the orchard, the variable rate fertilizer dispenser will then apply a new amount of fertilizer to the specific plant or specific region on the plant according to the updated variable rate fertilizer map.

Figure 5:
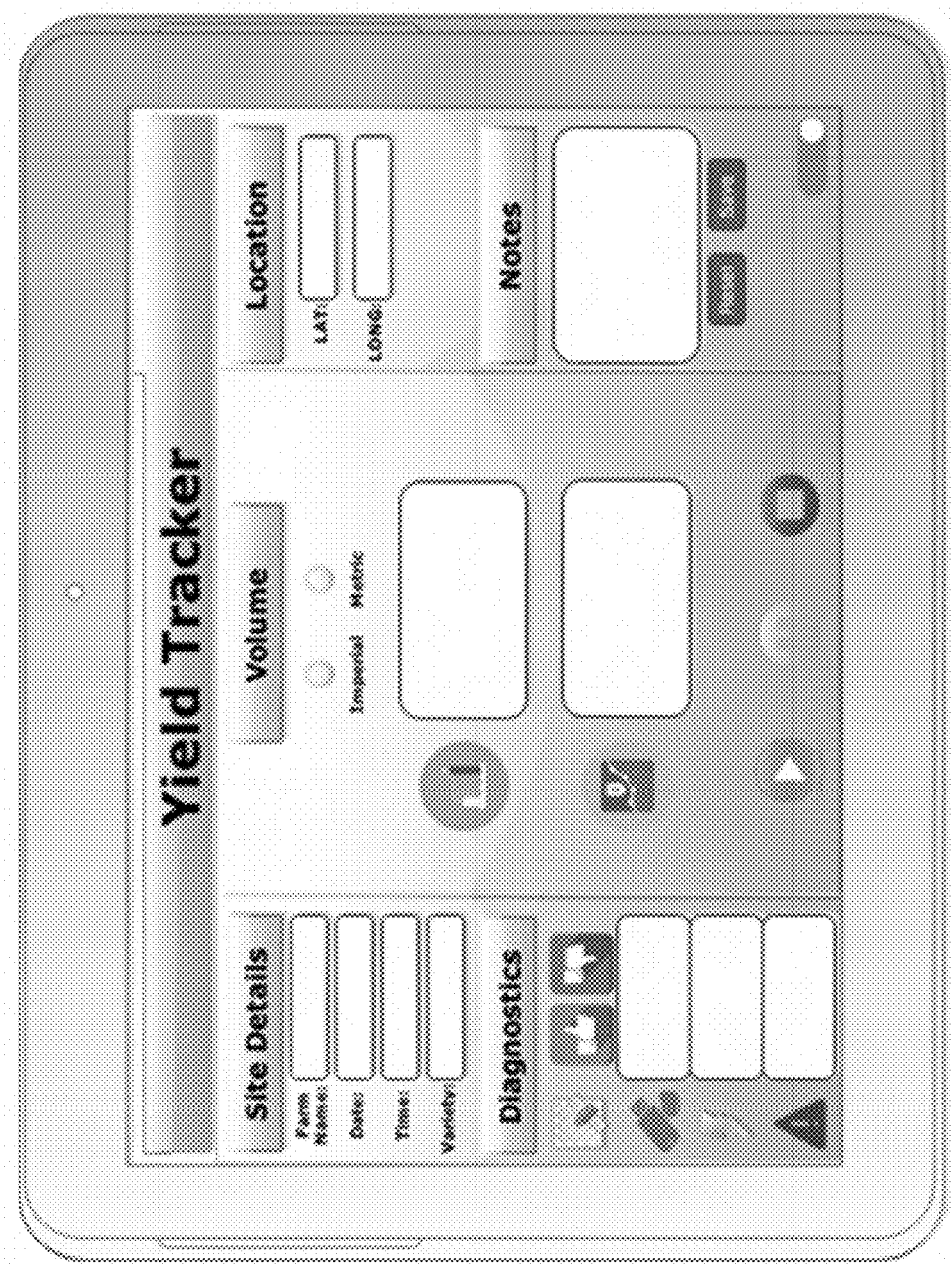
FIG. 5 shows a user interface for operating parts of the modular system according to embodiments of the invention.

In some embodiments, the modular system may include a user interface 150. An enlarged view of the user interface is further shown in FIG. 5. According to the exemplary embodiment shown in FIG. 5, the user interface may include icons and selectable buttons for controlling the collection of data and displaying the status of the data acquisition unit, transport vehicle, software, and hardware. For example, the user interface 150 may include a start button for beginning the collection of data, a stop button for stopping the recording of data, and an upload button for transferring the collected data to a post-processing server 106. The user interface 150 may also include icons for showing the speed of the collection vehicle 101, the status of cellular, or wireless connectivity of the modular processing unit's wireless transceiver 108, and the signal strength of the inertial navigation system's 105 GPS receivers. The user interface 150 may also include an icon that represents the height of the windrow 117 beneath the collection vehicle 101. In one aspect of the invention, if the user interface indicates that there is no cellular or wireless connectivity available, the modular processing unit 102 may temporarily buffer the fused data until a cellular or wireless signal becomes available again, upon which the modular processing unit 102 may transmit the data to the post-processing server 106. In some embodiments of the invention, the user interface 150 may include icons that indicate the fused data is in the process of being transmitted, that it has finished being transmitted, or that it has failed being transmitted. The user interface 150 may further include an input that allows a user to stop transmission.

In one aspect of the invention, the modular system be will effectively transparent to an operator of the collection vehicle 101. For example, once the system has been setup and calibrated, it may require little or no interaction from the operator to collect data.

Figure 6A:
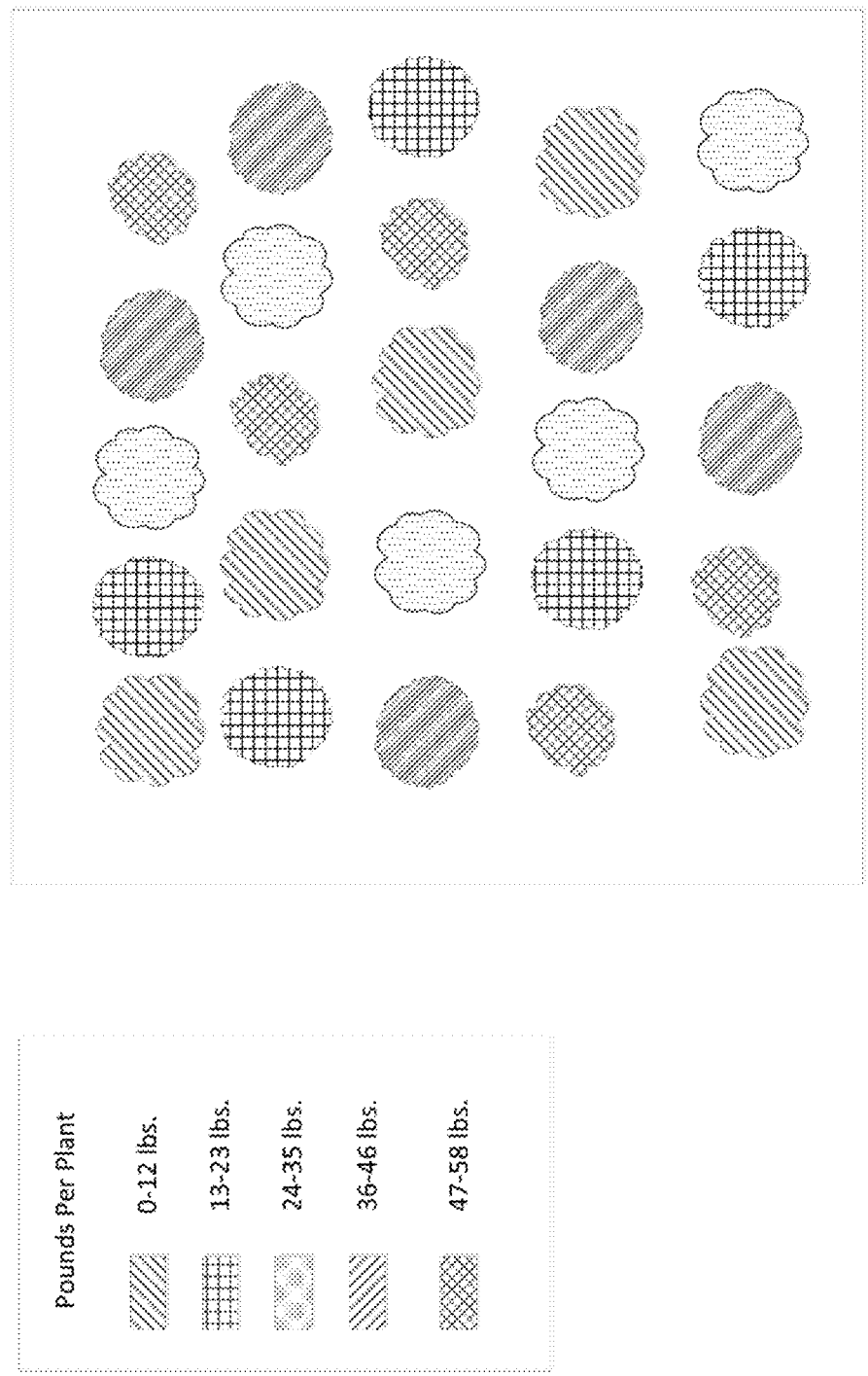
FIGS. 6A and 6B show a customer portal for rendering visualizations of the high-resolution geo-referenced data according to embodiments of the invention.
Figure 6B:
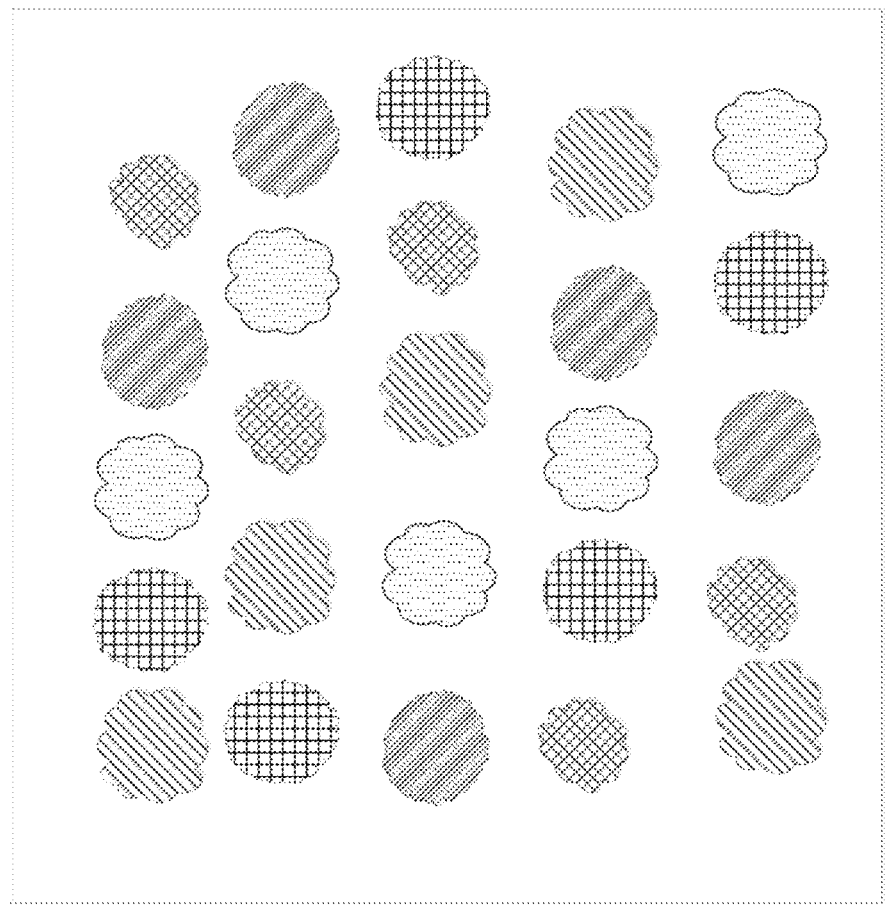
Figure 6B:
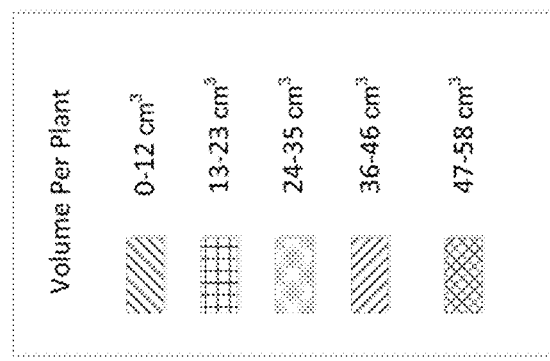

In some embodiments of the invention, the modular system may further include a customer portal 151. The customer portal 151 may be used to render visualizations of the data collected by the modular processing unit 102 and stored in the post-processing sever 106. For example, the visualization may include a map of the windrow volume calculations, a map of the windrow weight calculations, and a map of the three-dimensional point clouds. As described above, the map may render plants at a resolution of less than 1 meter, as well as their corresponding windrow volume and windrow weight calculations. For example, as shown in FIGS. 6A and 6B, each plant rendered on the map may visually indicate the aggregate weight or volume associated with that plant. In this way, the map may then be used to analyze the productivity of plants within the orchard or across a whole growing operation.

The customer portal 151 may further render a map of yield estimates at a resolution of less than 1 meter. As described above, the yield estimates may be calculated early in the growing season based on the three-dimensional point cloud data. These estimates may then be displayed on a map with the other calculations described above.

Figure 7:
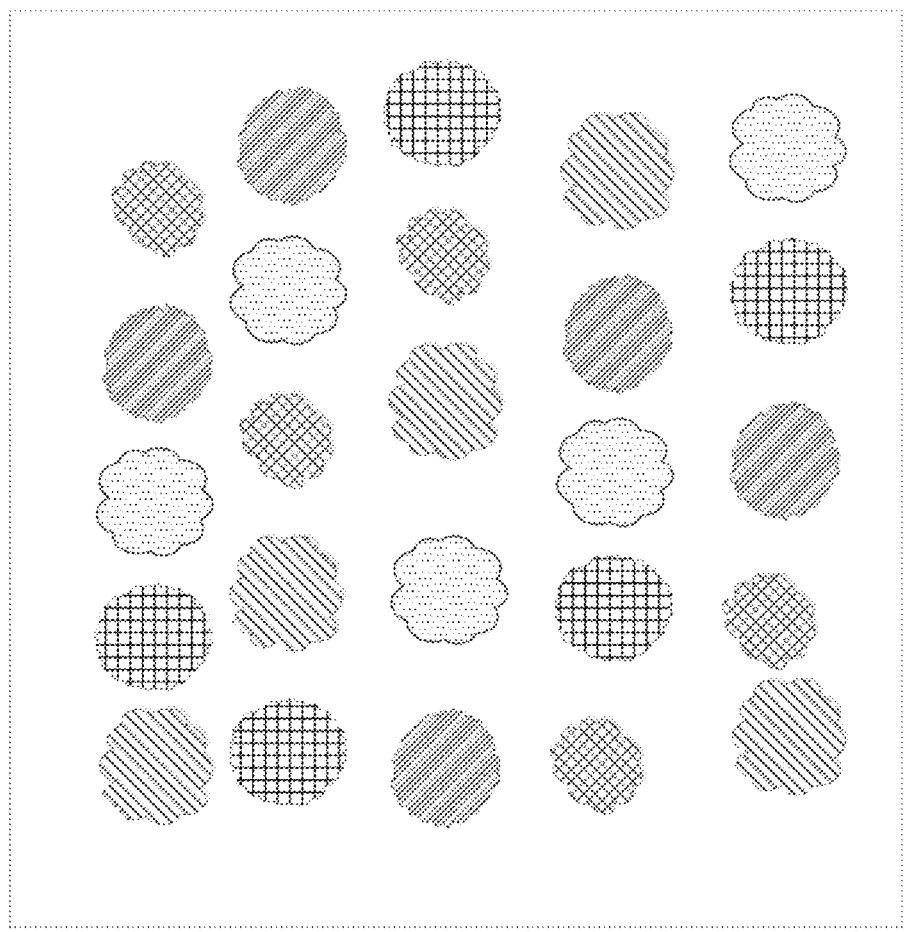
FIG. 7 shows a customer portal for rendering visualizations of the high-resolution geo-referenced data according to other embodiments of the invention.
Figure 7:
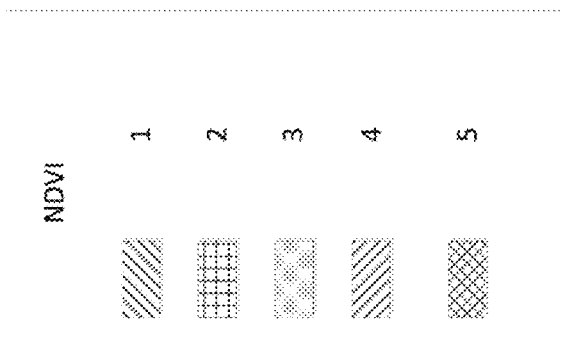

The modular system may further include a database that associates each three-dimensional point cloud representation of a plant with one or more layers of sensor data. The additional layers of sensor data may be for example, photographic, video, or spectral sensor data. Each of the one or more layers of sensor data may comprise a plurality of data points that are geo-referenced with the updated plurality of geodetic positions in the same manner as described above. Each data point in an additional layer of sensor data may be associated with one or more vertices of the three-dimensional point cloud. The customer portal may then be user to overlay the additional layers of sensor data on the three-dimensional point cloud. For example, as shown in FIG. 7, the NDVI may be generated based on spectral data collected by the vehicle. The NDVI data may then be overlaid on the same visualization of plant volume or weight data shown in FIGS. 6A and 6B, allowing agronomists to easily analyze correlations between yield and spectral data for each plant.

As another example, red, green, and blue (RGB) spectral band data obtained from a modular sensor such as a photographic camera, may be overlaid with three-dimensional point cloud data to precisely identify clusters of point cloud vertices that correspond to fruits or blossoms. In this way, the fusion of data additionally facilitates the sizing and counting of fruits or blossoms on a tree, thereby improving the prediction of a plant's yield. The photogrammetric data, three-dimensional point cloud data, and spectral and thermal imagery may also be used to analyze factors such as plant color, geometry, and texture. Statistical and analytic functions may be used to differentiate blossoms and fruits from leaves and branches.

Figure 8:
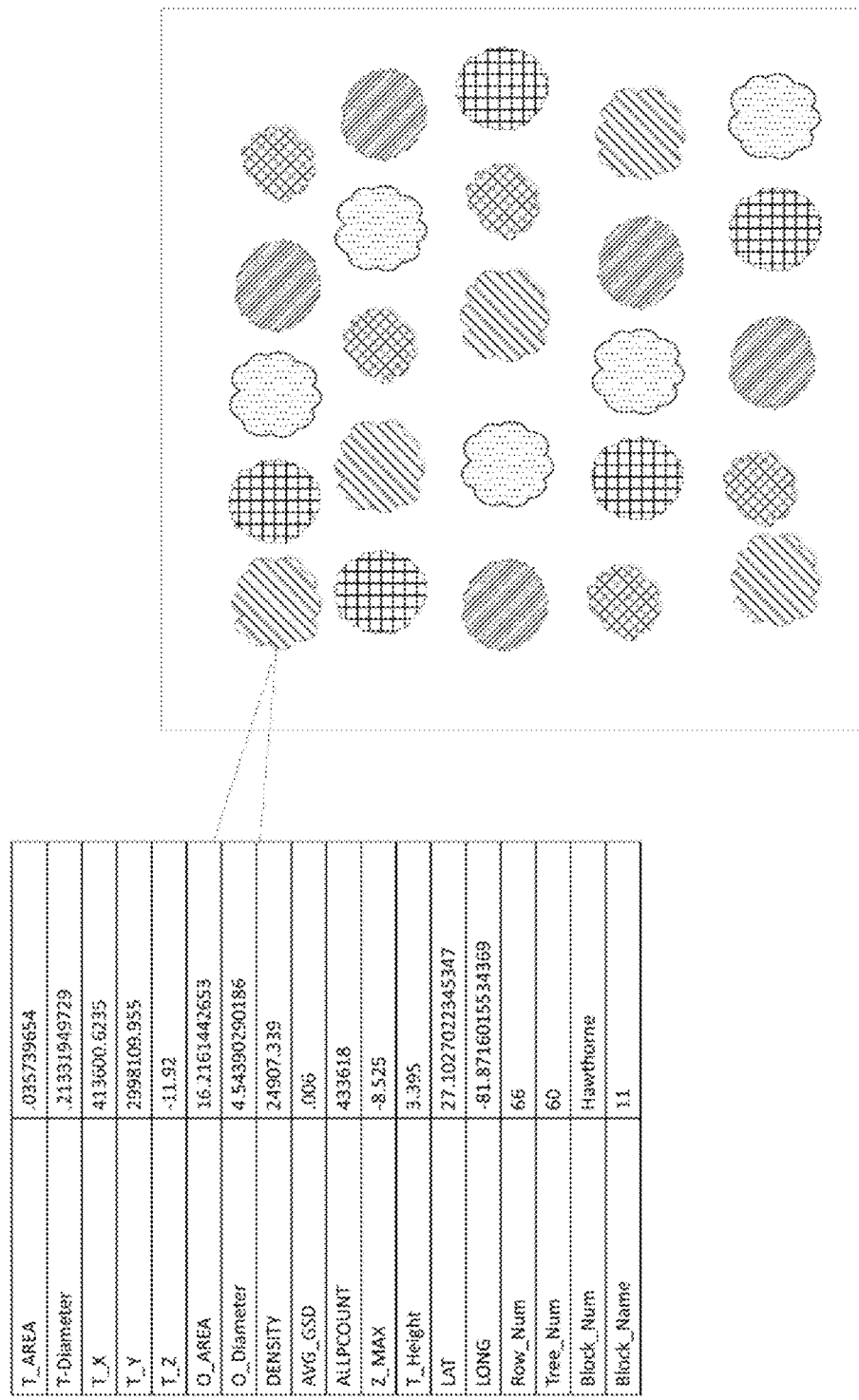
FIG. 8 shows a customer portal for rendering visualizations of the high-resolution geo-referenced data according to yet other embodiments of the invention.

In some embodiments of the invention, the customer portal 151 may allow a user to view and analyze the data and calculations that have been associated with a specific plant. For example, as shown in FIG. 8, a user may select a particular plant, triggering the customer portal 151 to display the data or subsets of data that have been calculated and associated with the plant. The data may include morphological attributes, such as its trunk diameter or area, as well as geodetic positional data such as the latitude and longitude of the plant's centroid.

The maps rendered in the customer portal 151 may be used to help agronomists and growers make decisions in regards to fertilizer practices, the amount of fertilizer, pesticides, irrigation, and other similar inputs or investments that are used in managing a growing operation. Similarly, the maps may be used to determine whether to completely remove an older, diseased, or less productive plants in favor of new "replants." For example, if the plant is diseased or too old such that fertilizer or pesticide would not improve its yield, the user can remove it altogether with a replant.

As described above, while the collection vehicle travels over the windrow, the sensor emits and detects pulses of light every distance d. These pulses of light are emitted across the cross-section of the windrow forming as a lateral scan. The pulses of light are reflected off the windrow and enable the first LiDAR sensor to calculate the distances from the first LiDAR sensor to the windrow. Other geometric aspects of the windrow may also be modeled using known dimensions of the first LiDAR sensor, the collection vehicle 101, and the windrow 117. As explained below, the sensor determines the distance to the windrow for a number of radial segments of specific widths and subtracts those measurements from the sensor height to approximate a curve representing the top of the windrow. The area under this curve is calculated by summing the area of each radial segment, and the volume is calculated by multiplying this area by the distance traveled between measurements.

Figure 2:
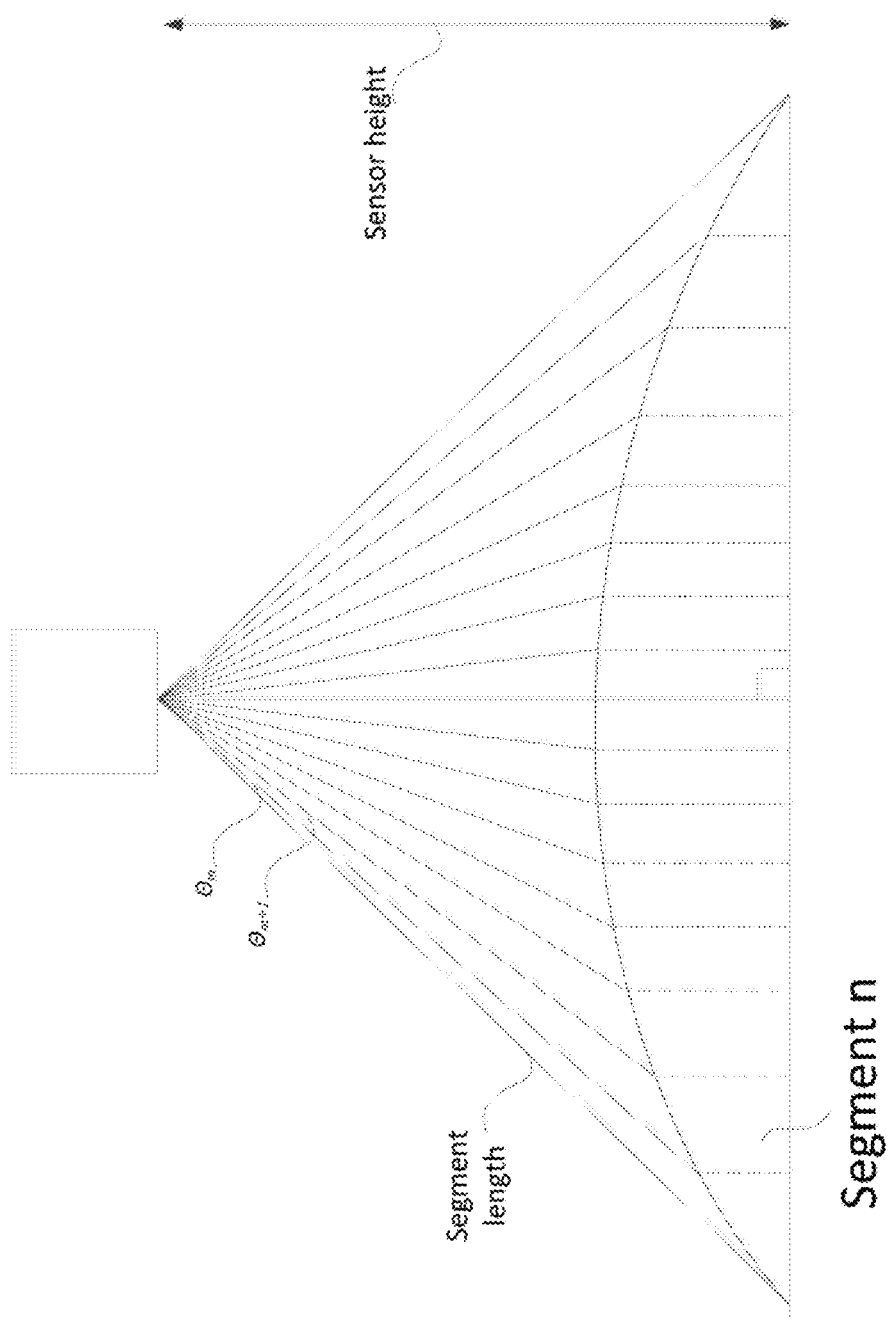
FIG. 2 shows a windrow segmented into a plurality of segments according to embodiments of the invention.
Figure 3:
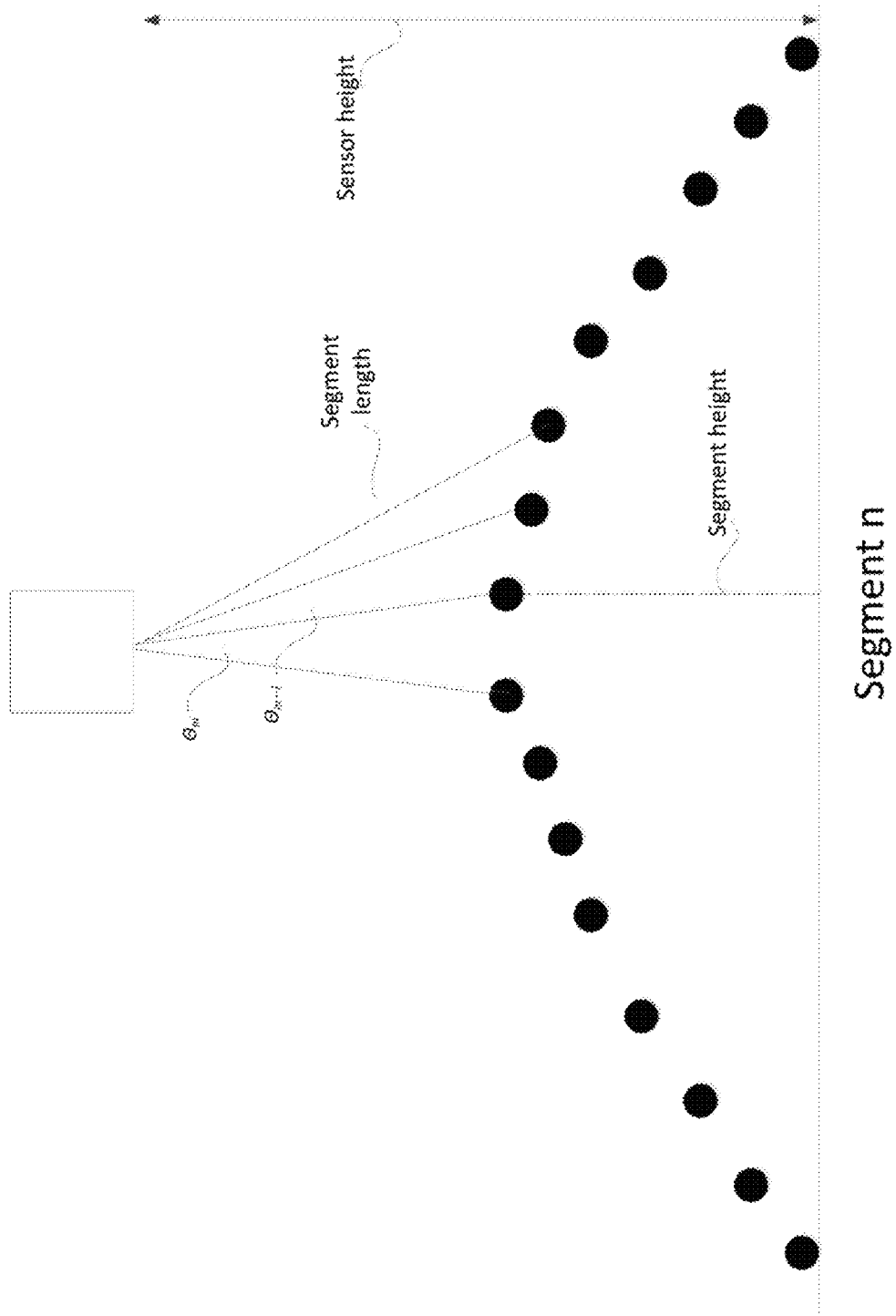
FIG. 3 shows segment lengths of a windrow as measured by a LiDAR sensor according to embodiments of the invention.
Figure 4:
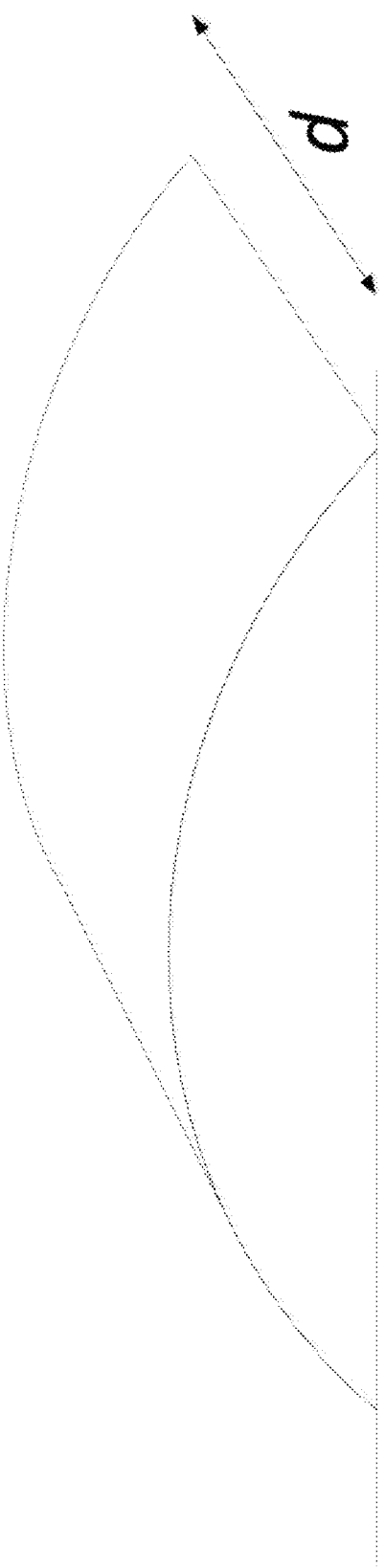
FIG. 4 shows the depth of a windrow portion according to embodiments of the invention.

As shown in FIGS. 2-4, the windrow may be partitioned into a plurality of segments n. In some embodiments of the invention, the windrow may be divided into sixteen, non-equal segments n, measured across the windrow as shown in FIGS. 2 and 3. There may be 8 non-equal segments on each side of a perpendicular plane intersecting the windrow. Each segment n is formed by a left edge and a right edge, having two angles, $\theta_m$ and $\theta_{m+1}$ with respect to the edge and an axis perpendicular from the sensor to the ground. The height of the segment above ground $H_n$ may be calculated by subtracting the distance between the sensor to the windrow from the height of the sensor above ground S. The height of the sensor above ground S may be a known constant that is determined when the first LiDAR sensor is mounted to the collection vehicle. The bisector of the angle formed between the left and right edge may be used to determine the segment height $H_n$ as follows:

$$H_n = S - (\cos((\theta_m + \theta_{m+1})/2) * R_n)$$

Where $R_n$ is the distance between the first LiDAR sensor and the surface of the windrow at segment n. The area of a segment n may then be calculated by multiplying the segment height $H_n$ by the segment's width $W_n$. The width $W_n$ for each segment may be determined as follows:

$$W_n = (\sin \theta_m * R_n) - (\sin \theta_{m+1} * R_n)$$

The area of each segment n may be added together to give the total cross-sectional area of the windrow at a particular point:

$$C_A = \sum_{N=1}^{i} H_n * W_n$$

Where $C_A$ is the cross-sectional area of the windrow and i is the total number of segments that form the windrow.

In other embodiments of the invention, the windrow may be modeled as a semi-cylinder. The cross-sectional $C_A$ area may thus be calculated as $\frac{1}{2} \times \pi \times r^2$. In some embodiments, r is the height of the center-most segment as calculated above. In other embodiments, r may be calculated as one half of the windrow width.

The volume of a portion of the windrow $V_p$ may be calculated by multiplying $C_A$ by the distance in between two lateral scans, d as shown in FIG. 4. In some embodiments of the invention, the distance d may be calculated based on the orthogonal velocity vectors of the collection vehicle and the frequency that the first LiDAR sensor emits a lateral scan. The distance d may thus be calculated as follows:

$$d = \frac{\sqrt{(Velocity\ X^2 + VelocityY^2 + Velocity\ Z^2)}}{Frequency}$$

Where VelocityX, VelocityY, and VelocityZ are the three orthogonal velocity vectors at each cycle, and Frequency is the frequency that the first LiDAR sensor emits a lateral scan. The total volume of the whole windrow in an orchard row may be calculated by summing each volume measurement $V_p$.

In some embodiments of the invention, the volume measurement system may be calibrated before each use by measuring a sample of zero volume over a distance of at least 100 meters. The data collected is processed using multiple linear regression to determine whether specific attributes measured by the sensor can be used to decrease the error seen in any final measurements. The expected range value of each segment is calculated using the measured sensor height at a known incident angle of each segment, and assuming a windrow height of zero. The difference between the theoretical value and the measured value for each segment is calculated for each sensor sweep. This variance from the expected value is regressed against other factors measured during the sweep, such as sensor pitch, sensor roll, and measured amplitude to determine how these conditions contribute to the overall error of measurements. The result of this regression is a series of coefficients which are subsequently used to calculate adjustments for each sensor sweep during the measurement phase, effectively correcting the ground height for any systematic errors stemming from the measurement equipment.

In another aspect of the invention, the first LiDAR sensor can also be used to measure the moisture content of the crop. Specifically, the LiDAR module may measure reflectance. Reflectance may be calculated using the following formula:

% Reflectance=Sample Amplitudes/Reference amplitudes*100

Sample Amplitudes are amplitude readings performed during a calibration of the first LiDAR sensor. A sample white reflective surface may be used for the calibration. The calibration may be performed by obtaining a reading of a sample surface at a fixed height. The above formula normalizes the sample readings to the reference surface and calculates a percentage of reflectance.

Figure 10:
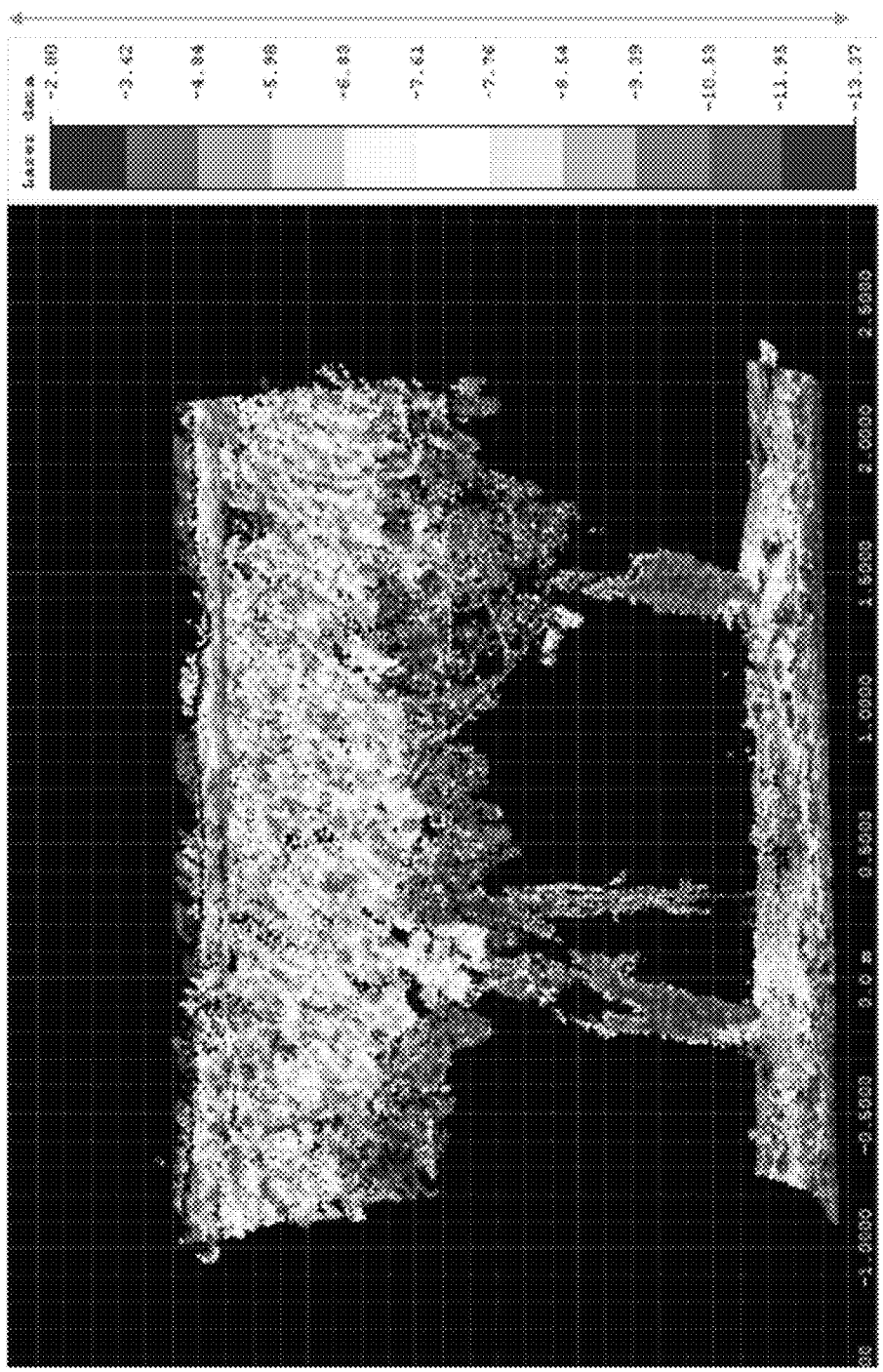
FIG. 10 shows a customer portal for rendering visualizations of the high-resolution geo-referenced reflectance data according to embodiments of the invention.

In one aspect of the invention, the reflectance within some of these wavelengths could be used as a substitute for the detection of moisture content. Specifically, higher reflectance in certain wavelengths indicates less moisture as the object scanned is reflecting more of the light back to the receiver optics. Further, lower reflectance R indicates an absorption of the wavelength, which therefore may indicate more moisture. The relationship between reflectance and moisture may be expressed by the following formulae:

$H_{A1}$=Lower reflectance(a-priori) %=more moisture $H_{A2}$=Higher reflectance(a-priori) %=less to no moisture Thus, lower reflectance may be correlated to higher moisture content, while high reflectance may be correlated to lower moisture content. Reflectance data may then be used to more accurately calculate the yield. For example, FIG. 10 shows an exemplary LiDAR reflectance image of plants rendered on the customer portal 151. The rendering shows that lower reflectance values appear in a canopy, where higher-moisture content objects such as leaves and fruit would appear.

The white surface reflectance value can be saved in a memory storage and called upon to normalize the raw amplitude data as it is collected and used to compute average reflectance.

In some embodiments of the invention, the average reflectance may be correlated to weight calculations. For example, high moisture may be correlated to high weight, and thus, lower reflectivity may correlate with higher weight.

The embodiments described in this disclosure can be combined in various ways. Any aspect or feature that is described for one embodiment can be incorporated into any other embodiment mentioned in this disclosure. Moreover, any of the embodiments described herein may be hardware-based, software-based and/or comprise a mixture of both hardware and software elements. Accordingly, while various novel features of the inventive principles have been shown, described and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps of any described methods may be carried out in different orders in many cases where such may be appropriate. Those skilled in the art will recognize, based on the above disclosure and an understanding therefrom of the teachings of the inventive principles, that the particular hardware and devices that are part of the system described herein, and the general functionality provided by and incorporated therein, may vary in different embodiments of the inventive principles. Accordingly, the particular system components are for illustrative purposes to facilitate a full and complete understanding and appreciation of the various aspects and functionality of particular embodiments of the present principles as realized in system and method embodiments thereof. Those skilled in the art will appreciate that the inventive principles can be practiced in other than the described embodiments, which are presented for purposes of illustration and not limitation.

I claim:

1. A modular system for improved real-time yield monitoring and sensor fusion of a crop in an orchard, the crop comprising one or more rows of one or more plants, the modular system comprising:
   a collection vehicle configured to transport a plurality of modular sensors through the one or more rows of one or more plants in the orchard;
   a modular processing unit mounted to the collection vehicle comprising a processor, a transceiver, a memory storage, a first clock, and a first communication port wherein the first clock generates a series of time-stamps;

a volume measurement module that measures the volume of a windrow formed in a row of the orchard, wherein the volume measurement module comprises a first Light Detection and Ranging ("LiDAR") sensor, a second communication port, and a second clock, wherein the volume measurement module is mounted to the collection vehicle and coupled to the modular processing unit by the first and second communication ports, wherein the collection vehicle is configured to transport the volume measurement module over the windrow and the volume measurement module is configured to:
  laterally scan the windrow formed in a row of the orchard every distance d traveled by the collection vehicle, wherein the lateral scan is an emission of a series of light pulses from the first LiDAR sensor,
  detect return echoes of the plurality of the series of light pulses,
  calculate a direct optical time-of-flight of the series of light pulses based on the time the light pulses were emitted and returned as echoes,
  determine a plurality of segment lengths based on the time-of-flight of the series of light pulses,
  calculate a volume of a windrow cross-section based on the plurality of segment lengths, wherein the plurality of segment lengths approximate the shape of the windrow surface along a cross-section of the windrow, and wherein the volume is calculated based on a cross-section area defined by the segments and the distance d,
  associate the volume of the windrow cross-section with a time-stamp generated by the second clock, and
  wherein the calculation of the volume of the windrow is performed in real-time as the volume measurement module is transported over the windrow;
a three-dimensional point-cloud scanning module comprising a second LiDAR sensor, a third clock, and a third communication port, wherein the three-dimensional point-cloud scanning module is mounted to the collection vehicle and coupled to the modular processing unit by the first and third communication ports, and wherein the second LiDAR sensor is configured to:
  assemble a three-dimensional point cloud representation of each plant in the orchard utilizing LiDAR, wherein the assembled three-dimensional point cloud comprises a plurality of three dimensional vertices that represent the external surface of each plant in the orchard, and
  associate the three-dimensional point cloud representation of each plant in the orchard with a time-stamp generated by the third clock;
an inertial navigation system that calculates a geodetic position of the collection vehicle, wherein the inertial navigation system comprises an Inertial Measurement Unit ("IMU"), a Global Positioning System ("GPS"), a fourth clock, and a fourth communication port, wherein the inertial navigation system is mounted to the collection vehicle and coupled to the modular processing unit by the first and fourth communication ports, wherein the inertial navigation system is transported through the row of the orchard by the collection vehicle, and wherein the inertial navigation system is configured to:
  calculate the geodetic position of the collection vehicle in real-time based on measurements received by the GPS and the IMU,
  calculate a velocity of the collection vehicle,
  calculate an attitude and heading of the collection vehicle, and
  associate each geodetic position calculated for the collection vehicle with a time-stamp that is generated by the fourth clock;
a post-processing server comprising a receiver and a processor that receives transmissions from the modular processing unit; and
a variable rate dispenser mounted to the collection vehicle and coupled to the modular processing unit, wherein the variable rate dispenser is configured to dispense an application at rate that dynamically varies based on a variable rate map and the position of the collection vehicle;
wherein the modular processing unit is configured to:
  control the volume measurement module, the three-dimensional point-cloud scanning module, and the inertial navigation system,
  receive a plurality of volume measurements and associated time-stamps from the volume measurement module,
  receive a plurality of geodetic positions and associated time-stamps from the inertial navigation system,
  receive a plurality of three-dimensional point cloud representations and associated time-stamps from the three-dimensional point-cloud scanning module,
  fuse the plurality of volume measurements, the plurality of geodetic positions, and the plurality of three-dimensional point cloud representations together into a fused data set, wherein the fusion is based on the associated time-stamps, and
  transmit, using the transceiver, the fused data set from the modular processing unit to the post-processing server;
wherein the post-processing server is configured to:
  receive the fused data set from the modular processing unit,
  identify a location where the inertial navigation system provided an inaccurate geodetic position,
  calculate a corrected geodetic position of the inertial navigation system based on the identified location,
  update the plurality of geodetic positions with the corrected geodetic position of the inertial navigation system,
  update the fused data set based on the updated plurality of geodetic positions,
  geo-reference the three-dimensional point cloud representations of each plant with the updated plurality of geodetic positions,
  cluster the geo-referenced three-dimensional point cloud representations of each plant;
  geo-reference the plurality of volume measurements with the updated plurality of geodetic positions
  associate the geo-referenced volume measurements to a plant in the orchard based on the proximity of the geo-referenced three-dimensional point cloud representations to the geo-referenced volume measurements;
  aggregate the geo-referenced volume measurements associated with the plant in the orchard;
  determine a total volume of crop produced by the plant in the orchard;
  verify an estimate of the yield of crop produced by the plant in the orchard using the determined total volume of the crop produced by the plant;
  identify an individual plant as underperforming based on the verification of the estimate of the yield;

target the underperforming plant with the variable rate dispenser based on three-dimensional point cloud data and geodetic position data to apply a higher dosage of fertilizer to the underperforming plant; and apply a higher dosage of fertilizer to the underperforming plant using the variable rate dispenser, the three-dimensional point cloud data, and the geodetic position data.

2. The system of claim 1, wherein the post-processing server is configured to create polygon mesh models derived from the geo-referenced three-dimensional point cloud representations.

3. The system of claim 1, wherein the clustered geo-referenced three-dimensional point cloud representations comprise a set of geo-referenced vertices.

4. The system of claim 3, wherein the one or more plants are grape vines and the set of geo-referenced vertices correspond to one or more grapes on the grape vines.

5. The system of claim 4, wherein the post-processing server is configured to identify grapes on the grape vines by performing a morphological analysis of the fused data set.

6. The system of claim 5, wherein the morphological analyses of the fused data set comprises searching for a boundary condition of the geo-referenced three-dimensional point-cloud representation.

7. The system of claim 6, wherein the morphological analyses of the fused data set further comprises identifying a plant canopy, and a plant trunk based on the boundary condition of the geo-referenced three-dimensional point cloud representation.

8. The system of claim 7, further comprising one or more modular sensors, wherein the one or more modular sensors are configured to measure at least one of red, green, and blue (RGB) spectral band data, multispectral data, hyperspectral data, thermal data, infrared data, radar data, ultrasonic data, and x-ray data, and
wherein the post-processing server is configured to display the data from the one or more modular sensors with the geo-referenced three-dimensional point cloud representation, and wherein the data from the one or more modular sensors aids in identifying clusters of point cloud vertices that correspond to fruits or blossoms.

9. The system of claim 3, wherein the post-processing server is configured to calculate a size of a clustered geo-referenced three-dimensional point cloud representation based on positional data of the set of geo-referenced vertices.

10. The system of claim 9, wherein the post-processing server is further configured to verify the calculated size of the clustered geo-referenced three-dimensional point cloud representation.

11. The system of claim 10, wherein the post-processing server is further configured to correct errors in the calculated size of the clustered geo-referenced three-dimensional point cloud representation.

12. The system of claim 9, wherein the post-processing server is further configured to calculate a size and number of grapes on the grape vines based on the clustered geo-referenced three-dimensional point cloud representations.

13. The system of claim 1, wherein the variable rate map targets a region on a plant of the one or more plants to treat with a dosage of application.

14. The system of claim 13, wherein the variable rate map is updated by the post-processing server based on spectral data.

15. The system of claim 14, wherein the one or more plants are grape vines and wherein the total yield measurement is determined by the post-processing server based on an aggregate windrow volume, and a calculation of size and number of grapes on the grape vines, the calculation based on the clustered geo-referenced three-dimensional point cloud representations.

16. A method for improved real-time yield monitoring and sensor fusion of a crop in an orchard using a collection vehicle configured to transport a plurality of modular sensors through one or more rows of plants in the orchard, the method comprising:
mounting a modular processing unit, a three-dimensional point-cloud scanning module, a volume measurement module that measures the volume of a windrow formed in a row of the orchard, an inertial navigation system, and a variable rate dispenser to a collection vehicle, wherein:
the modular processing unit comprises a processor, a transceiver, a memory storage, a first clock, and a communication port wherein the first clock generates a series of time-stamps,
the three-dimensional point-cloud scanning module comprises a LiDAR sensor, a second clock, and a communication port,
the inertial navigation system comprises an Inertial Measurement Unit ("IMU"), a Global Positioning System ("GPS"), a third clock, and a communication port;
the volume measurement module comprises a first Light Detection and Ranging ("LiDAR") sensor, a fourth clock and a communication port, is configured to laterally scan the windrow formed in a row of the orchard every distance d traveled by the collection vehicle, detect return echoes of the plurality of the series of light pulses, calculate a direct optical time-of-flight of the series of light pulses based on the time the light pulses were emitted and returned as echoes, determine a plurality of segment lengths based on the time-of-flight of the series of light pulses, and calculate a volume of a windrow cross-section based on the plurality of segment lengths, wherein the plurality of segment lengths approximate the shape of the windrow surface along a cross-section of the windrow, and wherein the volume is calculated based on a cross-section area defined by the segments and the distance d, associate the volume of the windrow cross-section with a time-stamp generated by the fourth clock, and wherein the calculation of the volume of the windrow is performed in real-time as the volume measurement module is transported over the windrow, and
the variable rate dispenser is configured to dispense an application at rate that dynamically varies based on a variable rate map and the position of the collection vehicle;
coupling the three-dimensional point-cloud scanning module, and the inertial navigation system to the modular processing unit;
collecting a three-dimensional point-cloud of each plant using a three-dimensional point cloud scanning module mounted on the collection vehicle, wherein the step of collecting a three-dimensional point-cloud of each plant comprises:
assembling a three-dimensional point cloud representation of each plant in the orchard utilizing Light Detection and Ranging ("LiDAR"), wherein the assembled three-dimensional point cloud comprises a plurality of three dimensional vertices that represent the external surface of each plant in the orchard, and associating the three-dimensional point cloud representation of each plant in the orchard with a time-stamp generated by the second clock, calculating a geodetic position of the collection vehicle, wherein the step of calculating the geodetic position of the collection vehicle comprises:

calculating the geodetic position of the collection vehicle in real-time based on measurements received by a Global Positioning System ("GPS") and an Inertial measurement Unit ("IMU") that are both part of an inertial navigation system mounted on the collection vehicle, calculating a velocity of the inertial navigation system, calculating an attitude and heading of the inertial navigation system, and associating each geodetic position calculated for the collection vehicle with a time-stamp that is generated by the third clock, processing data at a modular processing unit mounted on the collection vehicle, wherein the step of processing data at the modular processing unit comprises:

receiving a plurality of volume measurements and associated time-stamps from the volume measurement module, receiving a plurality of geodetic positions and associated time-stamps from the inertial navigation system, receiving a plurality of three-dimensional point cloud representations and associated time-stamps from the three-dimensional point-cloud scanning module, fusing the plurality of volume measurements, geodetic positions and three-dimensional point cloud representations together into a fused data set, wherein the fusion is based on the associated time-stamps, and transmitting the fused data set from the modular processing unit to a post-processing server; and post-processing transmissions received from the modular processing unit, wherein the step of post-processing transmissions received from the modular processing unit comprises:

receiving the fused data set from the modular processing unit, identifying a location where the inertial navigation system provided an inaccurate geodetic position, calculating a corrected geodetic position of the inertial navigation system based on the identified location, updating the plurality of geodetic positions with the corrected position of the inertial navigation system, updating the fused data set based on the updated plurality of geodetic positions, geo-referencing the three-dimensional point cloud representations of each plant with the updated plurality of geodetic positions, and clustering the geo-referenced three-dimensional point cloud representations of each plant, geo-referencing the plurality of volume measurements with the updated plurality of geodetic positions, associating the geo-referenced volume measurements to a plant in the orchard based on the proximity of the geo-referenced three-dimensional point cloud representations to the geo-referenced volume measurements, aggregating the geo-referenced volume measurements associated with the plant in the orchard, determining a total volume of crop produced by the plant in the orchard, verifying an estimate of the yield of crop produced by the plant in the orchard using the determined total volume of crop produced by the plant, identifying an individual plant as underperforming based on the verification of the estimate of the yield, targeting the underperforming plant with the variable rate dispenser based on three-dimensional point cloud data and geodetic position data to apply a higher dosage of fertilizer to the underperforming plant, and applying a higher dosage of fertilizer to the underperforming plant using the variable rate dispenser, the three-dimensional point cloud data, and the geodetic position data.

17. The method of claim 16, wherein the one or more plants are grape vines, and wherein the clustered geo-referenced three-dimensional point cloud representations comprise a set of geo-referenced vertices that correspond to one or more grapes on the grape vines.

18. The system of claim 17, further comprising the step of calculating a size of a clustered geo-referenced three-dimensional point cloud representation based on positional data of the set of geo-referenced vertices.

* * * * *